(12) United States Patent
Jure-Kunkel

(10) Patent No.: US 8,475,790 B2
(45) Date of Patent: Jul. 2, 2013

(54) COMBINATION OF CD137 ANTIBODY AND CTLA-4 ANTIBODY FOR THE TREATMENT OF PROLIFERATIVE DISEASES

(75) Inventor: Maria Jure-Kunkel, Plainsboro, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 13/122,630

(22) PCT Filed: Oct. 5, 2009

(86) PCT No.: PCT/US2009/059518
§ 371 (c)(1),
(2), (4) Date: Apr. 5, 2011

(87) PCT Pub. No.: WO2010/042433
PCT Pub. Date: Apr. 15, 2010

(65) Prior Publication Data
US 2011/0189189 A1    Aug. 4, 2011

Related U.S. Application Data

(60) Provisional application No. 61/103,023, filed on Oct. 6, 2008, provisional application No. 61/200,678, filed on Dec. 2, 2008.

(51) Int. Cl.
*A61K 39/395* (2006.01)

(52) U.S. Cl.
USPC ........................................... 424/130.1

(58) Field of Classification Search
None
See application file for complete search history.

(56) References Cited

U.S. PATENT DOCUMENTS

| | | | |
|---|---|---|---|
| 5,674,704 A | 10/1997 | Goodwin et al. | |
| 5,811,097 A | 9/1998 | Allison et al. | |
| 5,855,887 A | 1/1999 | Allison et al. | |
| 5,885,796 A | 3/1999 | Linley et al. | |
| 5,928,893 A | 7/1999 | Kang et al. | |
| 5,977,318 A | 11/1999 | Linley et al. | |
| 6,051,227 A | 4/2000 | Allison et al. | |
| 6,207,156 B1 | 3/2001 | Kuchroo et al. | |
| 6,210,669 B1 | 4/2001 | Aruffo et al. | |
| 6,303,121 B1 | 10/2001 | Kwon | |
| 6,355,476 B1 | 3/2002 | Kwon et al. | |
| 6,355,779 B1 | 3/2002 | Goodwin et al. | |
| 6,362,325 B1 | 3/2002 | Kwon | |
| 6,458,934 B1 | 10/2002 | Hong et al. | |
| 6,569,997 B1 | 5/2003 | Kwon | |
| 6,682,736 B1 | 1/2004 | Hanson et al. | |
| 6,887,673 B2 | 5/2005 | Kunkel et al. | |
| 6,905,685 B2 | 6/2005 | Kwon | |
| 6,974,863 B2 | 12/2005 | Kwon | |
| 6,984,720 B1 | 1/2006 | Korman et al. | |
| 7,109,003 B2 | 9/2006 | Hanson et al. | |
| 7,132,281 B2 | 11/2006 | Hanson et al. | |
| 7,138,500 B1 | 11/2006 | Goodwin et al. | |
| 7,211,259 B1 | 5/2007 | Goodwin et al. | |
| 7,214,493 B2 | 5/2007 | Kunkel et al. | |
| 7,235,555 B2 | 6/2007 | Evenou et al. | |
| 7,288,638 B2 | 10/2007 | Jure-Kunkel et al. | |
| 7,311,910 B2 * | 12/2007 | Linsley et al. | 424/130.1 |
| 7,611,702 B2 | 11/2009 | Fischkoff et al. | |
| 7,659,384 B2 | 2/2010 | Jure-Kunkel et al. | |
| 2002/0039581 A1 | 4/2002 | Carreno et al. | |
| 2002/0086014 A1 | 7/2002 | Korman et al. | |
| 2002/0168719 A1 | 11/2002 | Kwon | |
| 2003/0082157 A1 | 5/2003 | Kwon | |
| 2004/0091476 A1 | 5/2004 | Kwon | |
| 2004/0109847 A1 * | 6/2004 | Chen et al. | 424/85.4 |
| 2004/0241169 A1 | 12/2004 | Lowy et al. | |
| 2005/0095244 A1 | 5/2005 | Jure-Kunkel et al. | |
| 2005/0201994 A1 | 9/2005 | Korman et al. | |
| 2005/0202022 A1 | 9/2005 | Kunkel et al. | |
| 2005/0202028 A1 | 9/2005 | Ledbetter et al. | |
| 2006/0002904 A9 | 1/2006 | Kwon | |
| 2006/0029595 A1 | 2/2006 | Kwon | |
| 2006/0063923 A1 | 3/2006 | Kwon | |
| 2006/0110802 A1 | 5/2006 | Goodwin et al. | |
| 2006/0127985 A1 | 6/2006 | Goodwin et al. | |
| 2006/0171949 A1 | 8/2006 | Epstein et al. | |
| 2006/0182744 A1 | 8/2006 | Strome et al. | |
| 2007/0037826 A1 | 2/2007 | Evenou et al. | |
| 2007/0071675 A1 | 3/2007 | Wu et al. | |
| 2008/0118501 A1 | 5/2008 | Schindler et al. | |
| 2008/0286861 A1 * | 11/2008 | Fong et al. | 435/358 |
| 2010/0098701 A1 | 4/2010 | Jure-Kunkel et al. | |
| 2010/0183621 A1 | 7/2010 | Jure-Kunkel et al. | |
| 2010/0278828 A1 | 11/2010 | Jure-Kunkel | |
| 2012/0141494 A1 | 6/2012 | Jure-Kunkel et al. | |

FOREIGN PATENT DOCUMENTS

| | | |
|---|---|---|
| EP | 1212422 B1 | 2/2007 |
| WO | WO94/26290 | 11/1994 |
| WO | WO95/07984 | 3/1995 |
| WO | WO96/29348 | 9/1996 |
| WO | WO96/32495 | 10/1996 |

(Continued)

OTHER PUBLICATIONS

Wikipedia, accessed online on Mar. 26, 2012, two pages.*
NCBI Entrez Accession No. I12964.2 (gi:4337126), Schwarz, et al., Mar. 5, 1999.
Alegre, et al., "T-Cell Regulation by CD28 and CTLA-4", Nature Reviews, vol. 1, pp. 220-228 (2001).
Amezcua-Guerra, L.M., "Ulcerative colitis during CTLA-41g therapy in a patient with rheumatoid arthritis", Gut, vol. 55 (7), pp. 1059-1060 (2006).
Beck, et al., "Enterocolitis in Patients with Cancer after Antibody Blockade of Cytotoxic T-Lymphocyte-Associated Antigen 4", J Clin Oncology, vol. 24 (15), pp. 2283-2289 (2006).

(Continued)

*Primary Examiner* — Ilia Ouspenski
(74) *Attorney, Agent, or Firm* — Stephen C. D'Amico

(57) ABSTRACT

Compositions and methods are disclosed which are useful of the treatment and prevention of proliferative disorders.

8 Claims, 4 Drawing Sheets

FOREIGN PATENT DOCUMENTS

| | | |
|---|---|---|
| WO | WO98/16249 | 4/1998 |
| WO | WO98/42752 | 10/1998 |
| WO | WO99/09845 | 3/1999 |
| WO | WO99/36093 | 7/1999 |
| WO | WO00/34494 | 6/2000 |
| WO | WO0037504 | 6/2000 |
| WO | WO01/00207 A1 | 1/2001 |
| WO | WO01/00213 A1 | 1/2001 |
| WO | WO01/00214 A1 | 1/2001 |
| WO | WO01/14424 A2 | 3/2001 |
| WO | WO01/89567 A1 | 11/2001 |
| WO | WO01/95928 A2 | 12/2001 |
| WO | WO02/02638 A2 | 1/2002 |
| WO | WO02/069904 A2 | 9/2002 |
| WO | WO02/070007 A1 | 9/2002 |
| WO | WO03/055447 A2 | 7/2003 |
| WO | WO03/059269 A2 | 7/2003 |
| WO | WO03/084999 A1 | 10/2003 |
| WO | WO03/088991 A1 | 10/2003 |
| WO | WO2004/006853 A3 | 1/2004 |
| WO | WO2004/006950 A2 | 1/2004 |
| WO | WO2004/010947 A2 | 2/2004 |
| WO | WO2004/035607 A2 | 4/2004 |
| WO | WO2005/013958 A1 | 2/2005 |
| WO | WO2005/035584 A1 | 4/2005 |
| WO | WO2005/051321 A2 | 6/2005 |
| WO | WO2005/103081 A2 | 11/2005 |
| WO | WO2006/029220 A2 | 3/2006 |
| WO | WO2006/063067 A2 | 6/2006 |
| WO | WO2006/066568 A2 | 6/2006 |
| WO | WO2006/074399 A2 | 7/2006 |
| WO | WO2006/074399 A3 | 7/2006 |
| WO | WO2006/088447 A1 | 8/2006 |
| WO | WO2006/107101 A1 | 10/2006 |
| WO | WO2007/056539 A2 | 5/2007 |
| WO | WO2007/056539 A3 | 5/2007 |
| WO | WO2007/067959 A2 | 6/2007 |
| WO | WO2007/113648 A2 | 10/2007 |
| WO | WO2011/011027 A1 | 1/2011 |

OTHER PUBLICATIONS

Bretscher, et al., "A Theory of Self-Nonself Discrimination", Science, vol. 169, pp. 1042-1049 (1970).

Brunet, et al., "A new member of the immunoglobulin superfamily—CTLA-4", Nature, vol. 328, pp. 267-270 (1987).

Brunner, et al., "CTLA-4-Mediated Inhibition of Early Events of T Cell Proliferation", J of Immunology, vol. 162, pp. 5813-5820 (1999).

Camacho, et al., "Phase 1 Clinical trial of anti-CTLA4 human monoclonal antibody CP-675,206 in patients (pts) with advanced solid malignancies", J Clin Oncology, 2004 ASCO Annual Meeting Proceedings (Post-Meeting Edition), vol. 22, No. 14S (Jul. 15 Supplement), 2004, Abstract No. 2505.

Cong, et al., "Generation of Antigen-Specific, Foxp3-Expressing CD4+ Regulatory T Cells by Inhibition of APC Proteosome Function", J Immunology, vol. 174, pp. 2787-2795 (2005).

Daniel, et al., "FTY720 Ameliorates Th1-Mediated Colitis in Mice by Directly Affecting the Functional Activity of CD4+CD25+ Regulatory T Cells", J Immunology, pp. 2458-2468 (2007).

Davenport, et al., "Inhibition of pro-inflammatory cytokine generation by CTLA4-Ig in the skin and colon of mice adoptively transplanted with CD45RB$^{hi}$ CD4+ T cells correlates with suppression of psoriasis and colitis", International Immunopharmacology, vol. 2, pp. 653-672 (2002).

Foell, et al., "Engagement of the CD137 (4-1BB) costimulatory molecule inhibits and reverses the autoimmune process in collagen-induced arthritis and establishes lasting disease resistance", Immunology, vol. 113, pp. 89-98 (2004).

Foell, et al., "CD137-Mediated T Cell Co-Stimulation Terminates Existing Autoimmune Disease in SLE-Prone NZB/NZW F1 Mice", Ann. NY Acad. Sci., vol. 987, pp. 230-235 (2003).

Greenwald, et al., "CTLA-4 regulates cell cycle progression during a primary immune response", Eur J Immunology, vol. 32, pp. 366-373 (2002).

Gross, et al., "Identification and Distribution of the Costimulatory Receptor CD28 in the Mouse", vol. 149, pp. 380-388 (2) (1992).

Gurtner, et al., "CTLA-4-Ig Abrogates Tnbs Colitis by Inducing Indoleamine-2,3-Dioxygenase", Abstract No. 291, Gastroenterology, (Apr. 2005) vol. 128, No. 4, Suppl. 2, pp. A40. Meeting Info: Annual Meeting of the American-Gastroenterological-Association/Digestive-Disease-Week. Chicago, IL, USA. May 14-19, 2005.

Hamid, et al., "Advances in Immunotherapy for Melanoma", Medscape Hematology-Oncology, Article No. 577986 (2008).

Heward, et al., "Genetic susceptibility to the development of autoimmune disease", Clinical Science, vol. 93, pp. 479-491 (1997).

Holmen, et al., Gastroenterology, (Apr. 2005) vol. 128, No. 4, Suppl. 2, pp. A504. Meeting Info.: Annual Meeting of the American-Gastroenterological-Association/Digestive-Disease-Week. Chicago, IL, USA. May 14-19, 2005. Amer Gastroenterol Assoc.

Hou, et al., "CTLA-4 Gene Polymorphisms in Chinese Patients with Ulcerative Colitis", Inflamm Bowel Dis, vol. 11 (7), pp. 653-656 (2005).

Hou, et al., "Isolation and Characterization of Human CD4+CD25+ T Regulatory Cells for Early Phase Clinical Trials in Hematopoietic Cell Transplantation", Blood (ASH Annual Meeting Abstracts), 2005, 106:Abstract 1263.

Hurwitz, et al., "Combination Immunotherapy of Primary Prostate Cancer in a Transgenic Mouse Model Using CTLA-4 Blockade", Cancer Res., vol. 60, pp. 2444-2448 (2000).

Inagaki-Ohara, et al., "Suppressor of cytokine signaling 1 in lymphocytes regulates the development of intestinal inflammation in mice", Gut, vol. 55, pp. 212-219 (2006).

Izcue, et al., "Regulatory T cells suppress systemic and mucosal immune activation to control intestinal inflammation", vol. 212, pp. 256-271 (2006).

Jiang, et al. "Association between the cytotoxic T lymphocyte antigen-4 gene microsatellite polymorphism and inflammatory bowel diseases in the Chinese", Chinese journal of internal medicine, vol. 43, No. 3, pp. 491-494 (Mar. 2004) Abstract.

Jiang, et al., "Association of CTLA-4 Gene Microsatellite Polymorphism with Ulcerative Colitis in Chinese Patients", Inflamm Bowel Disease, vol. 12 (5), pp. 369-373 (2006).

Kapadia, et al., "CTLA-4 Blockade: Autoimmunity as Treatment", vol. 23 (35), pp. 8926-8928 (2005).

Kim, et al., "Paradoxical Effect of Reduced Costimulation in T Cell-Mediated Colitis", J Immunol, pp. 5563-5570 (2007).

Kim, et al., "Synergistic Costimulation by Both B7 Molecules Regulates Colitis Pathogenesis", Ann. NY Acad of Sci., vol. 1072, pp. 233-241 (2006).

Kocak, et al., "Combination Therapy with Anti-CTL Antigen-4 and Anti-4-1BB Antibodies Enhances Cancer Immunity and Reduces Autoimmunity", Cancer Res., vol. 66, pp. 7276-7284 (2006).

Kojima, et al., "Oxazolone-Induced Colitis in BALB/C Mice: a New Method to Evaluate the Efficacy of Therapeutic Agents for Ulcerative Colitis", J Pharmacol Sci, vol. 96, pp. 307-313 (2004).

Korman, et al., "Checkpoint Blockade in Cancer Immunotherapy", Advances in Immunology, vol. 90, pp. 297-339 (2006).

Krummel, et al., "CTLA-4 Engagement Inhibits IL-2 Accumulation and Cell Cycle Progression upon Activation of Resting T Cells", J Exp Med, vol. 183, pp. 2533-2540 (1996).

Jure-Kunkel, et al., "Combination of CTLA-4 Blockade and CD137 Agonist Enhances Antitumor Activity and Decreases Immune-related Adverse Events in Murine Models", Public Disclosure No. 1788; presented at the American Assoc. for Cancer Res Special Conference, Tumor Immunology:New Perspectives, Dec. 2-5, 2008; Miami, FL.

Lankarani, et al., "Analysis of cytotoxic T lymphocyte associated antigen 4 gene polymorphisms in patients with ulcerative colitis", J Gastroenterology and Hepatology, vol. 21, pp. 449-453 (2006).

Leach, et al., "Enhancement of Antitumor Immunity by CTLA-4 Blockade", Science, vol. 271, pp. 1734-1736 (1996).

Lee, et al., "Administration of agonistic anti-4-1BB monoclonal antibody leads to the amelioration of inflammatory bowel disease", Immunol Letters, vol. 101, pp. 210-216 (2005).

Li, et al., "Enhancement of NKT Cells and Increase in Regulatory T Cells Results in Improved Allograft Survival", J Surgical Research, vol. 134, pp. 10-21 (2006).

Lindsten, et al., "Characterization of CTLA-4 Structure and Expression on Human T Cells", J of Immunology, vol. 151 (7), pp. 3489-3499 (1993).

Linsley, et al., "CTLA-4 is a Second Receptor for the B Cell Activation Antigen B7", J Exp Med, vol. 174, pp. 561-569 (1991).

Linsley, et al., "Binding of the B Cell Activation Antigen B7 to CD28 costimulates T Cell Proliferation and Interleukin 2 mRNA Accumulation", J Exp Med, vol. 173, pp. 721-730 (1991).

Linsley, et al., "Human B7-1 (CD80) and B7-2 (CD86) Bind with Similar Avidities but Distinct Kinetics to CD28 and CTLA-4 Receptors", Immunity, vol. 1, pp. 793-801 (1994).

Liu, et al., "B7 Interactions with CD28 and CTLA-4 Control Tolerance or Induction of Mucosal Inflammation in Chronic Experimental Colitis", J. Immunol, vol. 167, pp. 1830-1838 (2001).

Liu, et al., "CD4+CD25+ Regulatory T Cells Cure Murine Colitis: The Role of IL-10, TGF-$\beta$, and CTLA4", J Immunol, vol. 171, pp. 5012-5017 (2003).

Liu, et al., "Differentiating role of B7-CD28/CTLA-4 interaction in the induction of mucosal inflammation and regulatory T cell functions in chronic experimental colitis", Univ Hosp Gasthuisberg, Univ of Leuven, Leuven, Belgium, Gastroenterology, (Apr. 2001) vol. 120, No. 5 Supplement 1, pp. A46-A47.

Liu, et al., "Blockade of CD28/CTLA-4-B7 Costimulatory Pathway in Colitic SCID Mice", Univ Hosp Gasthuisberg, Univ of Leuven, Leuven, Belgium, Gastroenterology, (Apr. 2000) vol. 118, No. 4 Suppl. 2 Part 1, pp. AGA No. A575.

Machida, et al., Association of polymorphic alleles of CTLA4 with inflammatory bowel disease in the Japanese, Work J. Gastroenterology, vol. 11 (27), pp. 4188-4193 (2005).

Maerten, et al., "Involvement of 4-1BB (CD137)-4-1BBligand interaction in the modulation of CD4+ T cell-mediated inflammatory colitis", Clin. Exp. Immunology, vol. 143, pp. 228-236 (2005).

Maerten, et al., "Functional expression of 4-1BB (CD137) in the inflammatory tissue in Crohn's disease", Clin Immunology, vol. 112, pp. 239-246 (2004).

Maerten, et al., "Induction of Tolerance by Blockade of CD40L and B71:studies in the T Cell Transfer Model of Colitis", Abstract No. T1567 Gastroenterology, (Apr. 2005) vol. 128, No. 4, Suppl. 2, pp. A505, Meeting Info: Annual Meeting of the American-Gastroenterological Association/Digestive-Disease-Week. Chicago, IL, USA. May 14-19, 2005.

Maerten, et al., "Role of CD137 (4-IBB) in the SCID T cell transfer colitis model" Digestive Disease Week Abstracts and Itinerary Planner, (2003) Abstract No. M1222. Meeting Info: Digestive Disease 2003. FL, Orlando, USA. May 17-22, 2003.; American Association for the Study of Liver Diseases; American Gastroenterological Association; American Society for Gastrointestinal Endoscopy; Society for Surgery of the Alimentary Tract.

Magyari, et al., "No association of the cytotoxic T-lymphocyte associated gene CTLA4 + 49A/G polymorphisms with Crohn's disease and ulcerative colitis in Hungarian population samples", World J. Gastroenterology, vol. 13 (15), pp. 2205-2208 (2007).

Makita, et al., "Intestinal Lamina Propria Retaining CD4+CD25+ Regulatory T Cells is a Suppressive Site of Intestinal Inflammation", J. Immunol, vol. 178, pp. 4937-4946 (2007).

McAdams, et al., "CTLA4-Ig Inhibits Development of Colitis More Effectively Than 5-ASA in C.B-17 SCID Mice Adoptively Transferred with Naïve T cells Isolated from B10.D2 Splenocytes", Gastroenterology, (Apr. 2001) vol. 120, No. 5 Supplement 1, pp. A.688; Meeting Info: 102nd Annual Meeting of the American Gastroenterological Association and Digestive Disease Week. Atlanta, Georgia, USA. May 20-23, 2001.

Mittler, et al., "Anti-CD137 Antibodies in the Treatment of Autoimmune Disease and Cancer", Immunologic Research, vol. 3, pp. 197-208 (2004).

Mokyr, et al., "Realization of the Therapeutic Potential of CTLA-4 Blockade in Low-Dose Chemotherapy-treated Tumor-bearing Mice", Cancer Research, vol. 58, pp. 5301-5304 (1998).

Morris, et al., "High Levels of Bacterial-Reactive Treg Activity in the Lamina Propria of Colitis-Resistant C57b1/6 Mice", Gastroenterology, (Apr. 2005) vol. 128, No. 4, Suppl. 2, pp. A614; Meeting Info.: Annual Meeting of the American-Gastroenterological-Association/Digestive-Disease-Week. Chicago, IL, USA. May 14-19, 2005.

Murillo, et al., "Therapeutic Antitumor Efficacy of Anti-CD137 Agonistic Monoclonal Antibody in Mouse Models of Myeloma", Clin Cancer Research, vol. 14, pp. 6895-6906 (2008).

Myers, et al., "Interfacing T-cell effector and regulatory function through CD137 (4-1BB) co-stimulation", TRENDS in Immunology, vol. 26 (8), pp. 440-446 (2005).

Nam, et al., "The Therapeutic Potential of 4-1BB (CD137) in Cancer", Current Cancer Drug Targets, vol. 5, pp. 357-363 (2005).

Phan, et al., "Cancer regression and autoimmunity induced by cytotoxic T lymphocyte-associated antigen 4 blockade in patients with metastatic melanoma", PNAS, vol. 100 (14), pp. 8372-8377 (2003).

Polese, et al., "Role of CD40 and B7 costimulators in inflammatory bowel diseases", Acta Bio Medica, vol. 74, Supp. 2, pp. 65-70 (2003).

Read, et al., "Cytotoxic T Lymphocyte-associated Antigen 4 Plays an Essential Role in the Function of CD25+CD4+ Regulatory Cells that Control Intestinal Inflammation", J Exp Med, vol. 192 (2), pp. 295-302 (2000).

Read, et al., "Blockade of CTLA-4 on CD4+CD25+ Regulatory T Cells Abrogates Their Function In Vivo", J. Immunol, vol. 177, pp. 4376-4383 (2006).

Ribas, et al., "Antitumor Activity in Melanoma and Anti-Self Responses in a Phase I Trial With the Anti-Cytotoxic T Lymphocyte-Associated Antigen 4 Monoclonal Antibody CP-675,206", J. Clin Oncology, vol. 23 (35), pp. 8968-8977 (2005).

Rosenbaum, J. T., "Emerging Biologic Therapies for Immune-Mediated Diseases", Ocular Pharmacology and Therapeutics—ISOPT, Proceedings of the International Symposium, 5th, Monte Carlo, Monaco, Mar. 11-14, 2004, 167-173 Publisher: Monduzzi Editore, Bologna, Italy.

Rueda, et al., "CTLA4/CT60 Polymorphism is Not Relevant in Susceptibility to Autoimmune Inflammatory Intestinal Disorders", Human Immunology, vol. 66, pp. 321-325 (2005).

Sato, et al., "Hyperexpression of Inducible Costimulator and Its Contribution on Lamina Propria T Cells in Inflammatory Bowel Disease", Gastroenterology, vol. 126, pp. 829-839 (2004).

Schwartz, R.H., "A Cell Culture Model for T Lymphocyte Clonal Anergy", Science, vol. 248, pp. 1349-1356 (1990).

Schwarz, et al., "A receptor induced by lymphocyte activation (ILA): a new member of the human nerve-growth-factor/tumor-necrosis-factor receptor family", Gene, vol. 134, pp. 295-298 (1993).

Seo, et al., "4-1BB-mediated immunotherapy of rheumatoid arthritis", vol. 10 (10), pp. 1088-1094 (2004).

Shuford, et al., "4-1BB Costimulatory Signals Preferentially Induce CD8+ T Cell Proliferation and Lead to the Amplification In Vivo of Cytotoxic T Cell Responses", J Exp Med, vol. 186 (1), pp. 47-55 (1997).

Singh, et al., "Control of intestinal inflammation by regulatory T cells", Immunological Reviews, vol. 182, pp. 190-200 (2001).

Stallmach, et al., "Modulation of gastrointestinal inflammation by chimeric proteins in experimental models", Z Gastrointestinal, vol. 38 (8), pp. 647-652 (2000) (Abstract).

Stenson, et al., "CTLA-4-Ig abrogates TNBS colitis by inducing the expression of indoleamine-2,3-dioxygenase", Gastroenterology, (Apr. 2005) vol. 128, No. 4, Suppl. 2, pp. A40. Meeting Info.: Annual Meeting of the American-Gastroenterological-Association/Digestive-Disease-Week. Chicago, IL, USA. May 14-19, 2005.

Strober, et al., "The Immunology of Mucosal Models of Inflammation", Annu Rev Immunol, vol. 20, pp. 495-549 (2002).

Sun, et al., "Immunotherapy with Agonistic Anti-CD137: Two Sides of a Coin", Cell Mol Immunology, vol. 1 (1), pp. 31-36 (2004).

Sun, et al., "Costimulatory molecule-targeted antibody therapy of a spontaneous autoimmune disease", Nature Medicine, vol. 8 (12), pp. 1405-1413 (2002).

Totsuka, et al., "Regulation of murine chronic colitis by CD4+CD25-PD-1+ regulatory T cells", Gastroenterology, (Apr. 2005) vol. 128, No. 4, Suppl. 2, pp. A56. Meeting Info.: Annual Meeting of the American-Gastroenterological-Association/Digestive-Disease-Week. Chicago, IL, USA. May 14-19, 2005.

Totsuka, et al., "Regulation of murine chronic colitis by CD4+CD25⁻ programmed death-1+ T cells", Eur J. Immunol, vol. 35, pp. 1773-1785 (2005).

Uraushihara, et al., "Regulation of Murine Inflammatory Bowel Disease by CD25+ and CD25− CD4+ Glucocorticoid-Induced TNF Receptor Family-Related Gene+ Regulatory T Cells", J Immunol, vol. 171, pp. 708-716 (2003).

Vandenborre, et al., "Human CTLA-4 is Expressed in Situ on T Lymphocytes in Germinal Centers, in Cutaneous Graft-versus-Host Disease, and in Hodgkin's Disease", Amer J Pathology, vol. 152 (4), pp. 963-973 (1998).

vanElas, et al., "Combination Immunotherapy of B16 Melanoma Using Anti-Cytotoxic T Lymphocyte-associated Antigen 4 (CTLA-4) and Granulocyte/Macrophage Colony-Stimulating Factor (GM-CSF)-producing Vaccines Induces Rejection of Subcutaneous and Metastatic Tumors Accompanied by Autoimmune Depigmentation", J. Exp Med, vol. 190 (3), pp. 355-366 (1999).

vanElas, et al., "Elucidating the Autoimmune and Antitumor Effector Mechanisms of a Treatment Based on Cytotoxic T Lymphocyte Antigen-4 Blockade in Combination with a B16 Melanoma Vaccine: Comparison of Prophylaxis and Therapy", J Exp Med, vol. 194 (4), pp. 481-489 (2001).

Walunas, et al.,"CTLA-4 Ligation Blocks CD28-dependent T Cell Activation", J. Exp Med, vol. 183, pp. 2541-2550 (1996).

Walunas, et al., "CTLA-4 Can Function as Negative Regulator of T Cell Activation", Immunity, vol. 1, pp. 405-413 (1994).

Watanabe, et al., "The Role of CTLA-4 on Regulatory T Cell Function in a Mouse Model of Microbially-Driven Inflammatory Bowel Disease", Gastroenterology, (Apr. 2006) vol. 130, No. 4, Suppl. 2, pp. A6 Abstract, Meeting Info.: Digestive Disease Week Meeting/107th Annual Meeting of the American-Gastroenterological-Association. Los Angeles, CA, USA. May 19-24, 2006.

Watts, Tania H., "TNF/TNFR Family Members in Costimulation of T Cell Responses", Annu Rev Immunol, vol. 23, pp. 23-68 (2005).

Zhou, et al, "Cytotoxic T lymphocyte antigen-4 promoter gene polymorphism is significantly associated with ulcerative colitis", Clin J Intern Med, vol. 45 (6), pp. 478-481 (Journal in Japanese, Abstract in English).

NCBI Entrez Accession No. AAA62478.2 (gi:4337127), Schwarz, et al., Mar. 5, 1999.

Hurwitz, et al., "CTLA-4 blockade synergizes with tumor-derived granulocyte-macrophage colony-stimulating factor for treatment of an experimental mammary carcinoma", PNAS, vol. 95, pp. 10067-10071 (1998).

\* cited by examiner

COMBINATION OF CD137 ANTIBODY AND CTLA-4 ANTIBODY FOR THE TREATMENT OF PROLIFERATIVE DISEASES

This application claims benefit to provisional application U.S. Ser. No. 61/103,023 filed Oct. 6, 2008; and to provisional application U.S. Ser. No. 61/200,678, filed Dec. 2, 2008; under 35 U.S.C. 119(e). The entire teachings of the referenced applications are incorporated herein by reference.

FIELD OF THE INVENTION

This invention relates to the fields of oncology and improved therapy regimens.

BACKGROUND OF THE INVENTION

The National Cancer Institute has estimated that in the United States alone, 1 in 3 people will be struck with cancer during their lifetime. Moreover, approximately 50% to 60% of people contracting cancer will eventually succumb to the disease. The widespread occurrence of this disease underscores the need for improved anticancer regimens for the treatment of malignancy.

Immunostimulatory monoclonal antibodies (mAb) represent a new and exciting strategy in cancer immunotherapy to potentiate the immune responses of the host against the malignancy (Melero et al., *Nat. Rev. Cancer*, 7:95-106 (2007)). Such agonistic or antagonistic mAbs bind to key receptors in cells of the immune system acting to enhance antigen presentation (e.g., anti-CD40), to provide costimulation (e.g., anti-CD137), or to counteract immunoregulation (e.g., anti-CTLA-4).

Ipilimumab is a human anti-human CTLA-4 antibody which blocks the binding of CTLA-4 to CD80 and CD86 expressed on antigen presenting cells and thereby, blocking the negative downregulation of the immune responses elicited by the interaction of these molecules.

CD137 (also called 4-1BB) is a T-cell costimulatory receptor induced on TCR activation (Nam et al., *Curr. Cancer Drug Targets*, 5:357-363 (2005); Watts et al., *Annu. Rev. Immunol.*, 23:23-68 (2005)). In addition to its expression on activated $CD4^+$ and $CD8^+$ T cells, CD137 is also expressed on $CD4^+$ $CD25^+$ regulatory T cells, natural killer (NK) and NK-T cells, monocytes, neutrophils, and dendritic cells. Its natural ligand, CD137L, has been described on antigen-presenting cells including B cells, monocyte/macrophages, and dendritic cells (Watts et al., *Annu. Rev. Immunol.*, 23:23-68 (2005)). On interaction with its ligand, CD137 leads to increased TCR-induced T-cell proliferation, cytokine production, functional maturation, and prolonged $CD8^+$ T-cell survival (Nam et al., *Curr. Cancer Drug Targets*, 5:357-363 (2005), Watts et al., *Annu. Rev. Immunol.*, 23:23-68 (2005)).

Many of the adverse events associated with ipilimumab treatment are a consequence of the intrinsic biological activity of ipilimumab, and its effects on T lymphocytes. The most common severe ($\geq$grade 3) immune-related adverse events (irAE) are gastrointestinal-related (12%). In general, these adverse immune events have been associated with clinical response (Phan et al., *Proc. Natl. Acad. Sci. USA*, 100:8372-8377 (2003), Beck et al., *J. Clin. Oncol.*, 24:2283-2289 (2006)), even in the absence of vaccination, suggesting that CTLA-4 blockade may be expanding autoreactive T cells. It has also been proposed that specific chemokine receptors expressed in the induced T cells may direct them to the intestine. Even though enterocolitis has been reported in melanoma subjects, administration of ipilimumab to healthy cynomolgus monkeys failed to detect this adverse event even after administration of multiple doses (unpublished results). Similarly, mice treated with multiple doses of CTLA-4 blocking antibodies did not develop clinical signs of colitis (Korman et al., *Adv. Immunol.*, 90:297-339 (2006)).

In the studies reported herein, mouse colitis models for ulcerative colitis and Crohn's-like disease were used to investigate the effect of CTLA-4 blockade in animals prone to develop immune-mediated colitis. The ultimate goal of these studies was to determine how treatment with CD137 agonist mAb could modulate the course of immune-mediated colitis in animals treated with CTLA-4 blocking mAb.

Two models were used in these studies: a) Oxazolone-induced colitis, a mixed Th1/Th2 colitis model that has a histological and cytokine-pattern similar to human ulcerative colitis; and b) Trinitrobenzene sulfonic acid (TNBS)-induced colitis, a Th1-mediated model of chronic intestinal inflammation that resembles Crohn's disease. The mouse model for ulcerative colitis is based on the application of oxazolone, a haptenating agent, which after intrarectal challenge, induces colitis in the distal portion of the colon with histopathological and immunological features that resemble the human disease (Strober et al., *Annu. Rev. Immunol.*, 20:495-549 (2002); Kojima et al., *J. Pharmacol. Sci.*, 96:307-313 (2004)). The model of Crohn's disease is based on the intrarectal delivery of trinitrobenzene sulfonic acid (TNBS). The intestinal inflammation is driven by IL-12 and is mediated by activation of macrophages and CD4+ T cell infiltration in the lamina propria (LP).

The present inventors have discovered for the first time, a treatment regimen involving the combination of an agonistic CD137 antibody with an anti-CTLA-4 inhibitor that results in a significant benefit for the treatment of colitis. It is an object of the invention to provide efficacious combination treatment regimens wherein an agonistic CD137 antibody agent is combined with one or more anti-CTLA4 agents for the treatment of colitis diseases.

SUMMARY OF THE INVENTION

The present invention provides a method for the treatment of proliferative disease comprising first administering to a mammal in need thereof an agonistic CD137 (4-1BB) antibody followed by a CTLA-4 antibody. In one aspect, the proliferative disease is one or more cancerous solid tumors. In another aspect, the proliferative disease is one or more refractory tumors. In another aspect, the proliferative disease is an inflammatory disorder, particularly colitis. In another aspect, the CTLA-4 antibody is ipilimumab or tremelimumab. In yet another aspect, the agonistic CD137 antibody is BMS-663513 (Bristol-Myers Squibb) or XmAb-5592 (Xencor).

The present invention provides a method for the treatment or prevention of drug-induced inflammatory conditions or immunotherapy-dependent inflammatory conditions, comprising first administering to a mammal in need thereof an agonistic CD137 (4-1BB) antibody followed by a CTLA-4 antibody. In one aspect, the inflammatory condition is colitis. In another aspect, the inflammatory condition is dermatitis, hepatitis, hypophysitis, enterocolitis, immunotherapy-dependent enterocolitis. In another respect, the inflammatory condition is associated with modulation of the immune system, particularly modulation of the co-stimulatory pathway, and preferably inhibition of CTLA4.

The present invention provides a method for the treatment or prevention of drug-associated weight loss or immunotherapy-dependent weight loss, comprising first administering to a mammal in need thereof an agonistic CD137 (4-1BB) antibody followed by a CTLA-4 antibody. In one aspect, the inflammatory condition is colitis. In another aspect, the inflammatory condition is dermatitis, hepatitis, hypophysitis, and enterocolitis. In one respect, the weight loss is associated with modulation of 4-1BB. In another respect, the weight loss is associated with modulation of the immune system, particularly modulation of the co-stimulatory pathway, and preferably inhibition of CTLA4.

The present invention provides a therapeutic regimen comprising: (i) the first administration of an agonistic CD137 antibody to a patient in need, and (ii) the subsequent administration of an anti-CTLA4 antibody; optionally comprising an interstitial period in-between said first and second administrations.

The present invention also provides a method of treatment comprising: (i) the sequential administration of an agonistic CD137 antibody to a patient in need, and (ii) the administration of an anti-CTLA4 antibody; optionally comprising an interstitial period in-between said first and second administrations.

The present invention also provides an alternative method of treatment comprising: (i) the administration of an anti-CTLA4 antibody, and (ii) the sequential administration of an agonistic CD137 antibody to a patient in need; optionally comprising an interstitial period in-between said first and second administrations.

The present invention also provides another alternative method of treatment comprising the simultaneous administration of: (i) an agonistic CD137 antibody to a patient in need, and (ii) the administration of an anti-CTLA4 antibody; optionally comprising an interstitial period in-between said first and second administrations.

Suitable anti-CTLA4 antagonist agents for use in the methods of the invention, include, without limitation, anti-CTLA4 antibodies, human anti-CTLA4 antibodies, mouse anti-CTLA4 antibodies, mammalian anti-CTLA4 antibodies, humanized anti-CTLA4 antibodies, monoclonal anti-CTLA4 antibodies, polyclonal anti-CTLA4 antibodies, chimeric anti-CTLA4 antibodies, MDX-010 (ipilimumab), tremelimumab, anti-CD28 antibodies, anti-CTLA4 adnectins, anti-CTLA4 domain antibodies, single chain anti-CTLA4 fragments, heavy chain anti-CTLA4 fragments, light chain anti-CTLA4 fragments, inhibitors of CTLA4 that agonize the co-stimulatory pathway, the antibodies disclosed in PCT Publication No. WO 2001/014424, the antibodies disclosed in PCT Publication No. WO 2004/035607, the antibodies disclosed in U.S. Published Application No. US 2005/0201994, and the antibodies disclosed in granted European Patent No. EP1212422B1. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. US 2002/0039581 and US 2002/086014. Other anti-CTLA-4 antibodies that can be used in a method of the present invention include, for example, those disclosed in: WO 98/42752; U.S. Pat. Nos. 6,682,736 and 6,207,156; Hurwitz et al., *Proc. Natl. Acad. Sci. USA,* 95(17):10067-10071 (1998); Camacho et al., *J. Clin. Oncology,* 22(145):Abstract No. 2505 (2004) (antibody CP-675206); Mokyr et al., *Cancer Res.,* 58:5301-5304 (1998), and U.S. Pat. Nos. 5,977,318, 6,682,736, 7,109,003, and 7,132,281.

Additional anti-CTLA4 antagonists include, but are not limited to, the following: any inhibitor that is capable of disrupting the ability of CD28 antigen to bind to its cognate ligand, to inhibit the ability of CTLA4 to bind to its cognate ligand, to augment T cell responses via the co-stimulatory pathway, to disrupt the ability of B7 to bind to CD28 and/or CTLA4, to disrupt the ability of B7 to activate the co-stimulatory pathway, to disrupt the ability of CD80 to bind to CD28 and/or CTLA4, to disrupt the ability of CD80 to activate the co-stimulatory pathway, to disrupt the ability of CD86 to bind to CD28 and/or CTLA4, to disrupt the ability of CD86 to activate the co-stimulatory pathway, and to disrupt the co-stimulatory pathway, in general from being activated. This necessarily includes small molecule inhibitors of CD28, CD80, CD86, CTLA4, among other members of the co-stimulatory pathway; antibodies directed to CD28, CD80, CD86, CTLA4, among other members of the co-stimulatory pathway; antisense molecules directed against CD28, CD80, CD86, CTLA4, among other members of the co-stimulatory pathway; adnectins directed against CD28, CD80, CD86, CTLA4, among other members of the co-stimulatory pathway, RNAi inhibitors (both single and double stranded) of CD28, CD80, CD86, CTLA4, among other members of the co-stimulatory pathway, among other anti-CTLA4 antagonists.

Each of these references is specifically incorporated herein by reference for purposes of description of CTLA-4 antibodies. A preferred clinical CTLA-4 antibody is human monoclonal antibody 10D1 (also referred to as MDX-010 and ipilimumab and available from Medarex, Inc., Bloomsbury, N.J.) is disclosed in WO 01/14424.

Suitable CD137 agonistic agents for use in the methods of the invention, include, without limitation, anti-CD137 antibodies, human anti-CD137 antibodies, mouse anti-CD137 antibodies, mammalian anti-CD137 antibodies, humanized anti-anti-CD137 antibodies, monoclonal anti-CD137 antibodies, polyclonal anti-CD137 antibodies, chimeric anti-CD137 antibodies, anti-4-1BB antibodies, anti-CD137 adnectins, anti-CD137 domain antibodies, single chain anti-CD137 fragments, heavy chain anti-CD137 fragments, light chain anti-CD137 fragments, the antibodies disclosed in U.S. Published Application No. US 2005/0095244, the antibodies disclosed in issued U.S. Pat. No. 7,288,638 (such as 20H4.9-IgG4 [10C7 or BMS-663513] or 20H4.9-IgG1 [BMS-663031]); the antibodies disclosed in issued U.S. Pat. No. 6,887,673 [4E9 or BMS-554271]; the antibodies disclosed in issued U.S. Pat. No. 7,214,493; the antibodies disclosed in issued U.S. Pat. No. 6,303,121; the antibodies disclosed in issued U.S. Pat. No. 6,569,997; the antibodies disclosed in issued U.S. Pat. No. 6,905,685; the antibodies disclosed in issued U.S. Pat. No. 6,355,476; the antibodies disclosed in issued U.S. Pat. No. 6,362,325 [1D8 or BMS-469492; 3H3 or BMS-469497; or 3E1]; the antibodies disclosed in issued U.S. Pat. No. 6,974,863 (such as 53A2); or the antibodies disclosed in issued U.S. Pat. No. 6,210,669 (such as 1D8, 3B8, or 3E1).

Additional CD137 agonistic antibodies are described in U.S. Pat. Nos. 5,928,893, 6,303,121 and 6,569,997.

Each of the anti-CTLA4 antagonist agents referenced herein may be administered either alone or in combination with a peptide antigen (e.g., gp100), either alone or in addition to an anti-proliferative agent disclosed herein.

The present invention further provides a pharmaceutical composition for the treatment of colitis which comprises a therapeutically effective amount of at least one (1) CD137 agonistic antibody and (2) an anti-CTLA4 antagonist.

In a preferred embodiment of the invention the anti-CTLA4 agent is administered simultaneously, concurrently, or preferably, subsequent to, the administration of an CD137 agonistic antibody or analogs thereof.

DETAILED DESCRIPTION OF THE INVENTION

Figure 1:
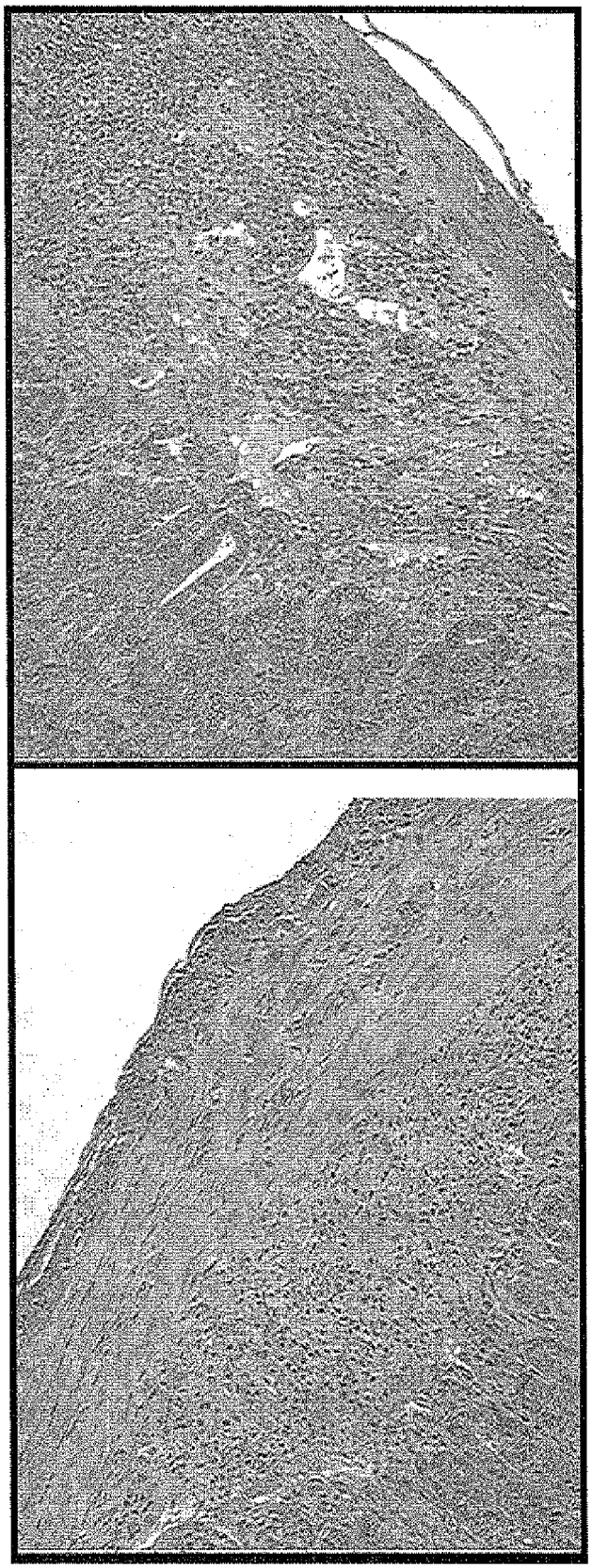
FIG. 1 shows the resulting colon morphology following treatment with anti-CTLA-4 mAb. Representative histological section of a control untreated mouse is provided in plate (A) and a representative histological section of a CTLA-4-treated mouse is provided in plate (B). Colon sections are shown with 10× magnification.

In accordance with the present invention, methods for the scheduled administration of one or more agonistic CD137 antibody agents in combination(s) with at least one anti-CTLA4 agent for the treatment and prevention of colitis diseases are provided.

Optimal T cell activation requires interaction between the T cell receptor and specific antigen (Bretscher, P. et al., *Science*, 169:1042-1049 (1970)) (the first signal) and engagement of costimulatory receptors on the surface of the T cell with costimulatory ligands expressed by the antigen-presenting cell (APC) (the second signal). Failure of the T cell to receive a second signal can lead to clonal anergy (Schwartz, R. H., *Science*, 248:1349-1356 (1990)). Two important T cell costimulatory receptors are CD28 and cytotoxic T lymphocyte-associated antigen 4 (CTLA-4, CD152) whose ligands on APC are B7-1 and B7-2 (Linsley, P. S. et al., *J. Exp. Med.*, 173:721-730 (1991); Linsley, P. S. et al., *J. Exp. Med.*, 174: 561-569 (1991)). Although CD28 and CTLA-4 are closely related members of the Ig superfamily (Brunet, J. F. et al., *Nature*, 328:267-270 (1987)), they function antagonistically. CD28 is constitutively expressed on the surface of T cells (Gross, J. A. et al., *J. Immunol.*, 149:380-388 (1992)), and upon engagement with B7-1 or B7-2, enhances the T cell receptor-peptide-MHC signal to promote T cell activation, proliferation, and IL-2 production (Linsley, P. S. et al., *J. Exp. Med.*, 173:721-730 (1991); Alegre, M. L. et al., *Nat. Rev. Immunol.*, 1:220-228 (2001)). CTLA-4 is not found on resting T cells but is up-regulated for 2-3 days after T cell activation (Lindsten, T. et al., *J. Immunol.*, 151:3489-3499 (1993), Walunas, T. L. et al., *Immunity*, 1, 405-413 (1994)). CTLA-4 also binds to B7-1 and B7-2 but with greater affinity than CD28 (Linsley, P. S. et al., *Immunity*, 1:793-801 (1994)) and antagonizes T cell activation, interferes with IL-2 production and IL-2 receptor expression, and interrupts cell cycle progression of activated T cells (Walunas, T. L. et al., *J. Exp. Med.*, 183:2541-2550 (1996); Krummel, M. F. et al., *J. Exp. Med.*, 183:2533-2540 (1996); Brunner, M. C. et al., *J. Immunol.*, 162:5813-5820 (1999); Greenwald, R. J. et al., *Eur. J. Immunol.*, 32:366-373 (2002)). The overall T cell response is determined by the integration of all signals, stimulatory and inhibitory.

Because CTLA-4 appears to undermine T cell activation, attempts have been made to block CTLA-4 activity in murine models of cancer immunotherapy. In mice implanted with immunogenic tumors, administration of anti-CTLA-4 Ab enhanced tumor rejection (Leach, D. R. et al., *Science*, 271: 1734-1736 (1996)), although little effect was seen with poorly immunogenic tumors such as SM1 mammary carcinoma or B16 melanoma. Enhanced antitumor immunity was seen when anti-CTLA-4 Ab was given with granulocyte-macrophage colony-stimulating factor (GM-CSF)-transduced B16 cell vaccine and was associated with depigmentation, suggesting that at least part of the antitumor response was antigen-specific against "self" melanocyte differentiation antigens (van Elsas, A. et al., *J. Exp. Med.*, 190:355-366 (1999); van Elsas, A. et al., *J. Exp. Med.*, 194:481-489 (2001)). In a transgenic murine model of primary prostate cancer, administrating anti-CTLA-4 Ab plus GM-CSF-expressing prostate cancer cells reduced the incidence and histological severity of prostate cancer and led to prostatitis in normal mice, again suggesting an antigen-specific immune response against self-antigens in tumor rejection (Hurwitz, A. A. et al., *Cancer Res.*, 60:2444-2448 (2000)). Furthermore, because many human tumor antigens are normal self-antigens, breaking tolerance against self may be critical to the success of cancer immunotherapy. The favorable tumor responses from CTLA-4 blockade in conjunction with tumor vaccines in murine models led to interest in using CTLA-4 blockade in human cancer immunotherapy.

An emerging approach for the treatment of cancer involves modulation of antitumor immune responses by treatment with monoclonal antibodies (mAb) to T cell costimulatory/co-inhibitory receptors, such as BMS-663513 (agonistic CD137 mAb), ipilimumab or tremelimumab (antagonistic CTLA-4 mAbs). While the studies described herein demonstrate the combination of CD137 and CTLA-4 antibodies results in efficacy in preclinical tumor models, it has been unknown whether such a combinatorial approach may result in exacerbation of immune-mediated adverse events.

In clinical trials, the most common adverse effect elicited by treatment with ipilimumab is immune-related colitis. The purpose of the studies presented herein was to examine the effect of the combination of an agonistic CD137 mAb (1 D8) and an antagonistic CTLA-4 mAb (UC10) in several murine tumor models, and in T-cell dependent experimental murine colitis models. In murine tumor models sensitive to one or both antibodies (P815 mastocytoma, SA1N fibrosarcoma and EMT-6 mammary carcinoma), simultaneous treatment with CTLA-4 and CD137 mAbs resulted in enhanced antitumor activity when compared to the activity of each agent alone. However, in models where neither mAb showed efficacy, the combination of both agents was ineffective (B16 melanoma). The potentiation of the antitumor activity was achieved when suboptimal doses of either agent were used in order to evaluate the effect of the combination in a setting in which maximal antitumor responses were not achievable by each agent alone. The effect of the combination in murine models of colitis was evaluated in the oxazolone-induced colitis, a mixed T helper 1 (Th1) and 2 (Th2) colitis model, and in the trinitrobenzene sulfonic acid (TNBS)-induced colitis, which is mainly driven by a Th1 response. CTLA-4 blockade elicited by mAb UC10 at doses shown to be active in tumor models (10-20 mg/kg) exacerbated the onset and severity of colitis in both models. Conversely, treatment with CD137 agonist 1D8 (5 mg/kg) ameliorated the symptoms and improved survival. Surprisingly, while concurrent treatment of CD137 and CTLA-4 mAbs did not improve or increase the detrimental effect of CTLA-4 blockade, treatment with CD137 mAb prior to CTLA-4 mAb markedly improved survival and prevented body weight loss compared to mice treated with CTLA-4 mAb alone ($p<0.05$). Thus, first treatment with an agonistic CD137 mAb, combined with the subsequent administration of an antagonistic CTLA-4 mAb improves the antitumor efficacy, reduces drug associated weight loss, and has beneficial effects in immune-mediated colitis.

Thus, in one embodiment, the therapeutic method of the invention comprises the combination of an agonistic CD137 antibody followed by the combination of one or more anti-CTLA4 agent(s) for the treatment of cancer, the treatment of cancer with diminished incidence of colitis and/or anti-CTLA4 agent induced colitis, and the treatment of colitis. The anti-CTLA4 agent(s) disclosed herein, when administered in combination with the administration of an agonistic CD137 antibody, demonstrated anti-tumor activity with no significant increase in the incidence of colitis in two murine colitis models.

Thus, in a preferred embodiment, the therapeutic method of the invention comprises the first administration of an agonistic CD137 antibody followed by the combination of one or more anti-CTLA4 agent(s) for the treatment of cancer, the treatment of cancer with diminished incidence of colitis and/or anti-CTLA4 agent induced colitis, and the treatment of colitis. The anti-CTLA4 agent(s) disclosed herein, when administered following the administration of an agonistic CD137 antibody, demonstrated superior anti-tumor activity with significantly diminished incidence of colitis in two murine colitis models.

The present invention also provides methods for reducing drug-associated weight loss, immune-mediated weight loss, weight loss associated with colitis, weight loss associated with immune-mediated colitis, and weight loss associated with anti-CTLA4 induced colitis.

The present invention also provides methods for the treatment of a variety of cancers, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, bone cancer, bone tumors, adult malignant fibrous histiocytoma of bone; childhood, malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma, chronic myeloid leukemia, acute lymphoblastic leukemia, philadelphia chromosome positive acute lymphoblastic leukemia (Ph+ ALL), multiple myeloma, acute myelogenous leukemia, chronic lymphocytic leukemia, mastocytosis and any symptom associated with mastocytosis, and any metastasis thereof. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, mast cell leukemia, in addition to other cancers. Other cancers are also included within the scope of disorders including, but are not limited to, the following: carcinoma, including that of the bladder, urothelial carcinoma, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma, and any metastasis thereof. Preferably, such methods of treating cancer with the treatment regimens of the present invention will result in a diminished incidence of anti-CTLA agent-induced colitis.

Other co-stimulatory pathway modulators of the present invention that may be used alone or in combination with other co-stimulatory pathway modulators disclosed herein, or in combination with other compounds disclosed herein include, but are not limited to, the following: agatolimod, belatacept, blinatumomab, CD40 ligand, anti-B7-1 antibody, anti-B7-2 antibody, anti-B7-H4 antibody, AG4263, eritoran, anti-OX40 antibody, ISF-154, and SGN-70; B7-1, B7-2, ICAM-1, ICAM-2, ICAM-3, CD48, LFA-3, CD30 ligand, CD40 ligand, heat stable antigen, B7h, OX40 ligand, LIGHT, CD70 and CD24.

Most preferably, the invention is used to treat colitis, Crohn's disease, anti-CTLA agent-induced colitis, and cancer.

In a preferred embodiment of this invention, a method is provided for the treatment of cancerous tumors. Advantageously, the method of this invention reduces the development of tumors, reduces tumor burden, or produces tumor regression in a mammalian host, with a concomitant decrease in the incidence of colitis and/or anti-CTLA agent-induced colitis or Crohn's disease.

Methods for the safe and effective administration of CD137 agonistic antibodies on one hand, or anti-CTLA4 antagonistic antibodies on the other, are individually known to those skilled in the art, but not in combination, and not in sequential combination in which an agonistic CD137 antibody is administered first, followed by the administration of an anti-CTLA4 antagonistic antibody. As one skilled in the art would appreciate, the individual administration of an agonistic CD137 antibody or an anti-CTLA4 antagonistic antibody is described in the standard literature.

The phrase "agonistic CD137 antibody" refers to anti-CD137 antibodies that bind mammalian 4-1BB and which result in an enhancement and stimulation of mammalian 4-1BB mediated, immune responses. Preferably, such antibodies bind to and agonize human 4-1BB. In addition, such antibodies preferably bind to mammalian 4-1BB and do not block the binding of the ligand for mammalian 4-1BB to H4-1BBL, thus permitting the binding of both an antibody and the ligand to mammalian 4-1BB.

The term "colitis" refers generally to a gastrointestinal inflammatory condition that results from activation, of the immune system. For the purposes of the present invention, colitis may be acute or chronic, ulcerative in nature or resulting from enterococcal or some other infection, or may be induced as a consequence of drug administration, including, but not limited to immune-mediated treatment, co-stimulatory pathway modulation, and CTLA4 inhibition.

The phrase "anti-CTLA agent-induced colitis" refers to a specific type of colitis that is caused, either directly or indirectly, by the inhibition of CTLA4.

As is known in the art, Ipilimumab refers to an anti-CTLA-4 antibody, and is a fully human $IgG_{1\kappa}$ antibody derived from transgenic mice having human genes encoding heavy and light chains to generate a functional human repertoire. Ipilimumab can also be referred to by its CAS Registry No. 477202-00-9, and is disclosed as antibody 10DI in PCT Publication No. WO 01/14424, incorporated herein by reference in its entirety and for all purposes. Specifically, Ipilimumab describes a human monoclonal antibody or antigen-binding portion thereof that specifically binds to CTLA4, comprising a light chain variable region and a heavy chain variable region having a light chain variable region comprised of SEQ ID NO:5, and comprising a heavy chain region comprised of SEQ ID NO:6. Pharmaceutical compositions of Ipilimumab include all pharmaceutically acceptable compositions comprising Ipilimumab and one or more diluents, vehicles and/or excipients. Examples of a pharmaceutical composition comprising Ipilimumab are provided in PCT Publication No. WO2007/67959. Ipilimumab may be administered by I.V.

Light Chain Variable Region for Ipilimumab:

```
                                            (SEQ ID NO: 5)
EIVLTQSPGTLSLSPGERATLSCRASQSVGSSYLAWYQQKPGQAPR

LLIYGAFSRATGIPDRFSGSGSGTDFTLTISRLEPEDFAVYYCQQY

GSSPWTFGQGTKVEIK
```

Heavy Chain Variable Region for Ipilimumab:

```
                                            (SEQ ID NO: 6)
QVQLVESGGGVVQPGRSLRLSCAASGFTFSSYTMHWVRQAPGKGL

EWVTFISYDGNNKYYADSVKGRFTISRDNSKNTLYLQMNSLRAED

TAIYYCARTGWLGPFDYWGQGTLVTVSS
```

As is known in the art, BMS-663513 refers to an anti-CD137 antibody, and is a fully human $IgG_4$ antibody derived from transgenic mice having human genes encoding heavy and light chains to generate a functional human repertoire. BMS-663513 is disclosed as antibody 1007 in U.S. Pat. No. 7,288,638, incorporated herein by reference in its entirety and for all purposes. Specifically, BMS-663513 describes a human monoclonal antibody or antigen-binding portion thereof that specifically binds to 4-1BB, comprising a light chain variable region and a heavy chain variable region, wherein: said light chain variable region comprises a CDR1 having amino acids 44-54 of SEQ ID NO:3, a CDR2 having amino acids 70-76 of SEQ ID NO:3, and a CDR3 having amino acids 109-119 of SEQ ID NO:3; and said heavy chain variable region comprises a CDR1 having amino acids 50-54 of SEQ ID NO:4, a CDR2 having amino acids 69-84 of SEQ ID NO:4, and a CDR3 having amino acids 117-129 of SEQ ID NO:4. Pharmaceutical compositions of BMS-663513 include all pharmaceutically acceptable compositions comprising BMS-663513 and one or more diluents, vehicles and/or excipients. BMS-663513 may be administered by I.V.

Light Chain Variable Region for BMS-663513:

```
                                            (SEQ ID NO: 3)
MEAPAQLLFLLLLWLPDTTGEIVLTQSPATLSLSPGERATLSCRA

SQSVSSYLAWYQQKPGQAPRLLIYDASNRATGIPARFSGSGSGTD

FTLTISSLEPEDFAVYYCQQRSNWPPALTFGGGTKVEIKRTVAAP
```

-continued

SVFIFPPSDEQLKSGTASVVCLLNNFYPREAKVQWKVDNALQSGN

SQESVTEQDSKDSTYSLSSTLTLSKADYEKHKVYACEVTHQGLSS

PVTKSFNRGEC

Heavy Chain Variable Region for BMS-663513:

(SEQ ID NO: 4)
MKHLWFFLLLVAAPRWVLSQVQLQQWGAGLLKPSETLSLTCAVYG

GSFSGYYWSWIRQSPEKGLEWIGEINHGGYVTYNPSLESRVTISV

DTSKNQFSLKLSSVTAADTAVYYCARDYGPGNYDWYFDLWGRGTL

VTVSSASTKGPSVFPLAPCSRSTSESTAALGCLVKDYFPEPVTVS

WNSGALTSGVHTFPAVLQSSGLYSLSSVVTVPSSSLGTKTYTCNV

DHKPSNTKVDKRVESKYGPPCPPCPAPEFLGGPSVFLFPPKPKDT

LMISRTPEVTCVVVDVSQEDPEVQFNWYVDGVEVHNAKTKPREEQ

FNSTYRVVSVLTVLHQDWLNGKEYKCKVSNKGLPSSIEKTISKAK

GQPREPQVYTLPPSQEEMTKNQVSLTCLVKGFYPSDIAVEWESNG

QPENNYKTTPPVLDSDGSFFLYSRLTVDKSRWQEGNVFSCSVMHE

ALHNHYTQKSLSLSLGK

As noted elsewhere herein, the administration of one or more anti-CTLA4 antagonists may be administered either alone or in combination with a peptide antigen (e.g., gp100), in addition to an anti-proliferative agent disclosed herein. A non-limiting example of a peptide antigen would be a gp 100 peptide comprising, or alternatively consisting of the sequence selected from the group consisting of: IMDQVPFSV (SEQ ID NO:1), and YLEPGPVTV (SEQ ID NO:2). Such a peptide may be administered orally, or preferably by injection s.c. at 1 mg emulsified in incomplete Freund's adjuvant (IFA) injected s.c. in one extremity, and 1 mg of either the same or a different peptide emulsified in IFA may be injected in another extremity.

The present invention also encompasses a pharmaceutical composition useful in the treatment of colitis, anti-CTLA agent-induced colitis, and cancer, comprising the sequential administration of a therapeutically effective amount of the combinations of this invention, with or without pharmaceutically acceptable carriers or diluents. The pharmaceutical compositions of this invention comprise the first administration of an agonistic CD137 agent and a pharmaceutically acceptable carrier, followed by an anti-CTLA4 agent or agents and a pharmaceutically acceptable carrier. The pharmaceutical compositions of this invention may also comprise an anti-CTLA4 agent or agents, an agonistic CD137 agent, and a pharmaceutically acceptable carrier. The methods entail the first administration of an agonistic CD137 agent and a pharmaceutically acceptable carrier, followed by an anti-CTLA4 agent or agents and a pharmaceutically acceptable carrier. The methods of this invention may also entail the use of an anti-CTLA4 agent or agents, an agonistic CD137 agent, and a pharmaceutically acceptable carrier.

The compositions of the present invention may further comprise one or more pharmaceutically acceptable additional ingredient(s) such as alum, stabilizers, antimicrobial agents, buffers, coloring agents, flavoring agents, adjuvants, and the like. The pharmaceutical compositions of the present invention may be administered orally or parenterally including the intravenous, intramuscular, intraperitoneal, subcutaneous, rectal and topical routes of administration.

For oral use, the pharmaceutical compositions of the present invention, may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc, and sugar. When aqueous suspensions are used for oral administration, emulsifying and/or suspending agents are commonly added.

In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic.

For preparing suppositories according to the invention, a low melting wax such as a mixture of fatty acid glycerides or cocoa butter is first melted, and the active ingredient is dispersed homogeneously in the wax, for example by stirring. The molten homogeneous mixture is then poured into conveniently sized molds and allowed to cool and thereby solidify.

Liquid preparations include solutions, suspensions and emulsions. Such preparations are exemplified by water or water/propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The pharmaceutical compositions of the present invention may also be delivered transdermally. The transdermal compositions can take the form of creams, lotions, aerosols and/or emulsions and can be included in a transdermal patch of the matrix or reservoir type as are conventional in the art for this purpose.

The combinations of the present invention may also be used in conjunction with other well known therapies that are selected for their particular usefulness against the condition that is being treated.

If formulated as a fixed dose, the active ingredients of the pharmaceutical combination compositions of the present invention are employed within the dosage ranges described below. Alternatively, the anti-CTLA4 agent, and the agonistic CD137 agent may be administered separately in the dosage ranges described below. In a preferred embodiment of the present invention, the anti-CTLA4 agent is administered in the dosage range described below following the administration of the CD137 agonistic agent in the dosage range described below.

The following sets forth preferred therapeutic combinations and exemplary dosages for use in the methods of the present invention.

| THERAPEUTIC COMBINATION | DOSAGE mg/m² (per dose) |
|---|---|
| First Administration of an Agonistic CD137 Antibody, followed by Administration of anti-CTLA4 Antibody | 0.01-15 mg/kg 0.1-15 mg/kg |
| Agonistic CD137 Antibody +anti-CTLA4 Antibody | 0.01-15 mg/kg 0.1-15 mg/kg |
| First Administration of an Agonistic CD137 Antibody, followed by Administration of anti-CTLA4 Antibody +anti-cancer vaccine(administered either before, after, or concurrently with the anti-CTLA4 antibody and/or agonistic CD137 antibody) | 0.01-15 mg/kg 0.1-15 mg/kg 0.001-100 mg |
| Agonistic CD137 Antibody +anti-CTLA4 Antibody +anti-cancer vaccine(administered either before, after, or concurrently with the anti-CTLA4 antibody and/or agonistic CD137 antibody) | 0.01-25 mg/kg 0.1-25 mg/kg 0.001-100 mg |

While this table provides exemplary dosage ranges of the agonistic CD137, anti-CTLA4, and anti-cancer vaccine agents, when formulating the pharmaceutical compositions of the invention the clinician may utilize preferred dosages as warranted by the condition of the patient being treated. The anti-CTLA4 antibody may preferably be administered at about 3-10 mg/kg, or the maximum tolerated dose. The anti-CTLA4 antibody may preferably be administered at about 0.3-10 mg/kg, or the maximum tolerated dose. In an embodiment of the invention, a dosage of CTLA-4 antibody is administered about every three weeks, about every four weeks, about every five weeks, or about every six weeks. Alternatively, the CTLA-4 antibody may be administered by an escalating dosage regimen including administering a first dosage of CTLA-4 antibody at about 3 mg/kg, a second dosage of CTLA-4 antibody at about 5 mg/kg, and a third dosage of CTLA-4 antibody at about 9 mg/kg. Likewise, the agonistic CD137 antibody may preferably be administered at about 0.1-1 mg/kg, or the maximum tolerated dose. Alternatively, the agonistic CD137 antibody may preferably be administered at about 0.1-10 mg/kg, or the maximum tolerated dose. In an embodiment of the invention, a dosage of agonistic CD137 antibody is administered about every three weeks, about every four weeks, about every five weeks, or about every six weeks. Alternatively, the agonistic CD137 antibody may be administered by an escalating dosage regimen including administering a first dosage of agonistic CD137 antibody at about 0.1 mg/kg to about 1 mg/kg, a second dosage of agonistic CD137 antibody at about 3 mg/kg, and a third dosage of agonistic CD137 antibody at about 9 mg/kg. Alternatively, the CD137 antibody may be administered at about 0.1 mg/kg to about 1 mg/kg every 3 weeks. Alternatively, the CD137 antibody may be administered at about 0.1 mg/kg to about 1 mg/kg every 6 weeks. Alternatively, the CD137 antibody may be administered at about 5 mg/kg every 6 weeks.

According to the present invention, a preferred therapeutic regimen comprises (i) the first administration of an agonistic CD137 antibody to a patient in need, (ii) the subsequent administration of an anti-CTLA4 antibody; and optionally comprising an interstitial period in-between said first and second administrations. In one aspect of the present invention, the interstitial period may be sequential. In another aspect of the present invention, the interstitial period may be immediately sequential. In another aspect of the present invention, the interstitial period may be about 1, about 2, about 3, about 4, about 5, about 6, about 7, about 8, about 9, about 10, about 15, about 20, about 25, about 30, about 35, about 40, about 45, about 50, about 55, or even about 60 minutes. In this context, the term "about" is construed to mean±1, 2, 3, 4, 5, 6, 7, 8, 9, or 10 minutes more or less than the stated amount. In another aspect of the present invention, the interstitial period may be about 12 to about 18 hours, or about 18 to about 24 hours. In another aspect of the present invention, the interstitial period may be about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, or even about 24 hours. In this context, the term "about" is construed to mean±1, 2, 3, 4, 5, 6, 7, 8, 9, 10, 11, or 12 hours more or less than the stated amount. In another aspect of the present invention, the interstitial period may be about 1, about 2, about 3, about 4, about 5, about 6, or about 7 days. In this context, the term "about" is construed to mean±1, 2, 3, 4, 5, 6, or 7 days more or less than the stated amount.

Additional dosing and therapeutic regimens for CD137 agonistic antibodies are disclosed in U.S. Pat. No. 6,210,669 and are incorporated herein in their entirety for all purposes.

In another specific embodiment, the escalating dosage regimen includes administering a first dosage of CTLA-4 antibody at about 3 or 5 mg/kg and a second dosage of CTLA-4 antibody at about 5 or 9 mg/kg.

Further, the present invention provides an escalating dosage regimen, which includes administering an increasing dosage of CTLA-4 antibody about every six weeks.

In another specific embodiment, the escalating dosage regimen includes administering a first dosage of agonistic CD137 antibody at about 3 or 5 mg/kg and a second dosage of agonistic CD137 antibody at about 5 or 9 mg/kg.

Further, the present invention provides an escalating dosage regimen, which includes administering an increasing dosage of agonistic CD137 antibody about every six weeks.

In an aspect of the present invention, a stepwise escalating dosage regimen is provided, which includes administering a first CTLA-4 antibody dosage of about 3 mg/kg, a second CTLA-4 antibody dosage of about 3 mg/kg, a third CTLA-4 antibody dosage of about 5 mg/kg, a fourth CTLA-4 antibody dosage of about 5 mg/kg, and a fifth CTLA-4 antibody dosage of about 9 mg/kg. In another aspect of the present invention, a stepwise escalating dosage regimen is provided, which includes administering a first dosage of 5 mg/kg, a second dosage of 5 mg/kg, and a third dosage of 9 mg/kg.

According to the present invention, all recited doses and/or escalating dosing regimens individually listed for an anti-CTLA-4 antibody or individually listed for an agonistic CD137 antibody are intended to follow a regimen comprising the sequential administration of a first administration of an agonistic CD137 antibody, an interstitial period, followed by the administration of an anti-CTLA-4 antibody.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

Certain cancers can be treated effectively with one or more CD137 agonistic agents and a one or more anti-CTLA4 agents, preferably with the first administration of a CD137 agonistic agent followed by one or more anti-CTLA4 agents. Such triple and quadruple combinations can provide greater efficacy. When used in such triple and quadruple combinations the dosages set forth above can be utilized.

When employing the methods or compositions of the present invention, other agents used in the modulation of tumor growth or metastasis in a clinical setting, such as antiemetics, can also be administered as desired.

The present invention encompasses a method for the treatment of colitis, anti-CTLA agent-induced colitis, and cancer wherein a CD137 agonistic agent and an anti-CTLA4 agent are administered sequentially or simultaneously. Thus, while a pharmaceutical formulation comprising a CD137 agonistic and an anti-CTLA4 agent(s) may be advantageous for administering the combination for one particular treatment, prior administration of the anti-CTLA4 agent(s) may be advantageous in another treatment, or the simultaneous administration of the anti-CTLA4 agent(s) may be advantageous in another treatment. It is also understood that the instant combination of one or more CD137 agonistic agents with one or more anti-CTLA4 agent(s) may be used in conjunction with other methods of treating colitis and cancer (preferably cancerous tumors) including, but not limited to, radiation therapy and surgery. It is further understood that a cytostatic or quiescent agent, if any, may be administered sequentially or simultaneously with any or all of the other therapies.

The combinations of the instant invention may also be co-administered with other well known therapeutic agents that are selected for their particular usefulness against the condition that is being treated. Combinations of the instant invention may alternatively be used sequentially with known pharmaceutically acceptable agent(s) when a multiple combination formulation is inappropriate.

The CD137 agonistic agent(s) and anti-CTLA4 agent(s) can be administered according to therapeutic protocols well known in the art. It will be apparent to those skilled in the art that the administration of the CD137 agonistic agent(s) and anti-CTLA4 agent(s) can be varied depending on the disease being treated and the known effects of the agent(s) on that disease. Also, in accordance with the knowledge of the skilled clinician, the therapeutic protocols (e.g., dosage amounts and times of administration) can be varied in view of the observed effects of the administered therapeutic agents (i.e., anti-CTLA4 agent(s), CD137 agonistic agent(s)) on the patient, and in view of the observed responses of the disease to the administered therapeutic agents.

In the methods of this invention, one or more CD137 agonistic agent(s) is administered simultaneously or sequentially with one or more anti-CTLA4 agent(s). Thus, it is not necessary that the anti-CTLA4 therapeutic agent(s) and CD137 agonistic agent be administered simultaneously or essentially simultaneously. The advantage of a simultaneous or essentially simultaneous administration is well within the determination of the skilled clinician. Preferably, the one or more CD137 agonistic agent(s) is administered first followed by the administration of one or more anti-CTLA4 agent(s).

Also, in general, the one or more CD137 agonistic agent(s), and anti-CTLA4 agent(s) do not have to be administered in the same pharmaceutical composition, and may, because of different physical and chemical characteristics, have to be administered by different routes. For example, the one or more CD137 agonistic agent(s) may be administered intravenously to generate and maintain good blood levels thereof, while the anti-CTLA4 agent(s) may also be administered intravenously. Alternatively, the one or more CD137 agonistic agent(s) may be administered orally to generate and maintain good blood levels thereof, while the anti-CTLA4 agent(s) may also be administered intravenously. Alternatively, the one or more CD137 agonistic agent(s) may be administered intravenously to generate and maintain good blood levels thereof, while the anti-CTLA4 agent(s) may be administered orally. Alternatively, the one or more CD137 agonistic agent(s) may be administered orally to generate and maintain good blood levels thereof, while the anti-CTLA4 agent(s) may be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of one or more CD137 agonistic agent(s) and anti-CTLA4 agent(s) will depend upon the diagnosis of the attending physicians and their judgment of the condition of the patient and the appropriate treatment protocol.

If the compound of one or more CD137 agonistic agent(s) and the anti-CTLA4 agent(s) are not administered simultaneously or essentially simultaneously, then the initial order of administration of the one or more CD137 agonistic agent(s) and the anti-CTLA4 agent(s) may be varied. Thus, for example, the one or more CD137 agonistic agent(s) may be administered first followed by the administration of the anti-CTLA4 agent(s); or the anti-CTLA4 agent(s) may be administered first followed by the administration of the one or more CD137 agonistic agent(s). This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the anti-CTLA4 agent(s) may be administered initially. Preferably, for example, the one or more CD137 agonistic agent(s) may be administered initially. The treatment is then continued with the administration of the anti-CTLA4 agent(s) or CD137 agonistic agent(s), as the case may be, and thereof and optionally followed by administration of a cancer vaccine alone or in combination with a cytostatic agent, if desired, until the treatment protocol is complete. Alternatively, the administration of the one or more CD137 agonistic agent(s) thereof and optionally followed by administration of a cytostatic agent may be administered initially. The treatment is then continued with the administration of the anti-CTLA4 agent(s), until the treatment protocol is complete.

Thus, in accordance with experience and knowledge, the practicing physician can modify each protocol for the administration of a component (therapeutic agent—i.e., one or more CD137 agonistic agent(s), anti-CTLA4 agent(s)), of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

In order to facilitate a further understanding of the invention, the following examples are presented primarily for the purpose of illustrating more specific details thereof. The scope of the invention should not be deemed limited by the examples, but to encompass the entire subject matter defined by the claims.

REFERENCES

Phan, G. Q. et al., "Cancer regression and autoimmunity induced by cytotoxic T lymphocyte-associated antigen 4 blockade in patients with metastatic melanoma", *Proc. Natl. Acad. Sci. USA*, 100:8372-8377 (2003).

Beck, K. E. et al., "Enterocolitis in patients with cancer after antibody blockade of cytotoxic T-lymphocyte-associated antigen 4", *J. Clin. Oncol.*, 24:2283-2289 (2006).

Ipilimumab Nonclinical Toxicology Written Summary, Bristol-Myers Squibb Research and Development, August 2008, BMS Document Control Number 930023101.

Korman, A. J. et al., "Checkpoint blockade in cancer immunotherapy", *Adv. Immunol.*, 90:297-339 (2006), Review.

Strober, W. et al., "The immunology of mucosal models of inflammation", *Annu. Rev. Immunol.*, 20:495-549 (2002).

Kojima, R. et al., "Oxazolone-induced colitis in BALB/C mice: a new method to evaluate the efficacy of therapeutic agents for ulcerative colitis", *J. Pharmacol. Sci.*, 96:307-313 (2004).

Walunas, T. L. et al., "CTLA-4 can function as a negative regulator of T cell activation", *Immunity*, 1(5):405-413 (August 1994).

Shuford, W. W. et al., "RS.4-1BB costimulatory signals preferentially induce CD8+ T cell proliferation and lead to the amplification in vivo of cytotoxic T cell responses", *J. Exp. Med.*, 186(1):47-55 (Jul. 7, 1997).

Foell, J. et al., "CD137-mediated T cell co-stimulation terminates existing autoimmune disease in SLE-prone NZB/NZW F1 mice", *Ann. NY Acad. Sci.*, 987:230-235 (April 2003).

Sun, Y. et al., "Costimulatory molecule-targeted antibody therapy of a spontaneous autoimmune disease", *Nat. Med.*, 8:1405-4413 (2002).

Foell, J. L. et al., "Engagement of the CD137 (4-1BB) costimulatory molecule inhibits and reverses the autoimmune process in collagen-induced arthritis and establishes lasting disease resistance", *Immunology*, 113(1):89-98 (September 2004).

Seo, S. K. et al., "4-1BB-mediated immunotherapy of rheumatoid arthritis", *Nat. Med.*, 10:1088-1094 (2004).

Example 1

Method of Assessing the Effect of the Combination of CD137 Agonistic Antibodies with Anti-CTLA4 Blockage on Tumor Growth in Murine Colitis Models Background The antitumor activity of a homolog of ipilimumab, a CTLA-4 blocking agent, was investigated in combination with CD137 agonistic antibodies, in preclinical studies. CD137 agonism can ameliorate the development of autoimmunity in many experimental mouse models of autoimmune disease, whereas CTLA-4 blocking mAb promotes expansion and infiltration of tumor-primed cytolytic T cells.

The inventors hypothesized that this combinatorial approach may produce therapeutic synergy based on their unique mechanism of action and cellular targets in preclinical tumor models.

An emerging approach for the treatment of cancer involves modulation of antitumor immune responses by treatment with monoclonal antibodies to T cell co-stimulatory/co-inhibitory receptors, CD137 agonistic mAb, and ipilimumab (CTLA-4 blocking mAb). In some preclinical models, combination of CD137 and CTLA-4 antibodies resulted in improved efficacy. However, it is unknown whether this combinatorial approach may result in exacerbation of immune-mediated adverse events. In clinical trials, the most common adverse effect elicited by treatment with ipilimumab is immune-related colitis. The purpose of the studies presented here was to examine the effect of the combination of a CD137 agonistic mAb and an anti-CTLA-4 mAb in T-cell dependent experimental murine colitis models.

Methods

Two models were evaluated: a) oxazolone-induced colitis, a mixed T helper (Th)1/Th2 colitis model; and b) trinitrobenzene sulfonic acid (TNBS)-induced colitis, which is mainly driven by a Th1 response. Since ipilimumab and BMS-663513 do not recognize mouse CTLA-4 and CD137 respectively, evaluation of their preclinical activity in mouse models has been conducted with anti-mouse CTLA-4 and anti-mouse CD137 antibodies.

Results

Results from these studies showed that CTLA-4 blockade elicited by mAb UC10 at doses shown to be active in tumor models (10-20 mg/kg) exacerbated the onset and severity of the disease. Conversely, treatment with CD137 agonist BMS-469492 (5 mg/kg) ameliorated the symptoms and improved survival. Furthermore, while concurrent treatment of CD137 and CTLA-4 mAbs did not improve or increase the detrimental effect of CTLA-4 blockade, treatment with CD137 mAb prior to CTLA-4 mAb markedly improved survival and prevented body weight loss compared to mice treated with CTLA-4 blocking mAb alone (p<0.05).

Conclusions

Thus, treatment with a CD137 mAb prior to CTLA-4 blockade reduces the severity of immune-mediated colitis elicited by a CTLA-4 blocking mAb.

Example 2

Method of Assessing Whether a Murine Oxazolone-Induced Colitis could be Used as a Model to Study the Effect of Immunomodulatory Agents Materials and Methods Antibodies The hybridoma for the anti-CTLA-4 monoclonal antibody (mAb), clone 4F10-UC10 (hamster IgG anti-mouse CTLA-4) (Walunas et al., *Immunity*, 1(5):405-413 (August 1994)) was obtained from the American Tissue Type Collection (Manassas, Va.), and assigned as BMS-863019. BMS-469492 (clone 1D8) is a rat $IgG_{2a}$ with specificity to mouse CD137 (Shuford et al., *J Exp Med.*, 186(1):47-55 (Jul. 7, 1997)). Both antibodies were produced and purified by BMS (Protein Therapeutics Division, Hopewell, N.J., USA), and certified to have <0.5 EU/mg endotoxin levels, >95% purity and <5% high molecular weight species. Stock solutions of both antibodies were kept at −80° C. and were thawed out at 4° C. prior to use. Control antibodies consisted of a polyclonal hamster IgG or rat immunoglobulins (Jackson ImmunoResearch, West Grove, Pa.). Dosing solutions of antibodies were prepared per study in sterile phosphate buffered saline (pH 7.0).

Animals

Six-week old (18-22 g) SJL/J male mice were purchased from Charles River Labs, (Wilmington, Mass.). All animal test protocols were subjected to IACUC approval and conform to USDA requirements. Food and water were supplied ad libitum.

In Vivo Oxazolone-Induced Colitis

SJL/J mice had a 2×2 cm field of abdominal skin shaved and were pre-sensitized by epicutaneous application of 150 µl of 3% oxazolone (4-ethoxymethylene-2-phenyl-2oxazolin-5-one, Sigma, St Louis, Mo.) in 100% ethanol, on day 0. Five days after skin sensitization, mice were placed under general anesthesia with isofluorane (Halocarbon Labs, River Edge, N.J.) and rechallenged with intrarectal administration of 100 µl of 0.75% oxazolone in 50% ethanol or 50% ethanol vehicle alone (as a procedural control), through a 3.5 F catheter (Braintree Scientific, Braintree, Mass.) inserted 4 cm proximal to the anal verge. Disease progression was evaluated daily by monitoring survival and body weight. At the end of each study mice were sacrificed and the colons excised. Colon lengths were then recorded. Treatments were administered as described in Section 3 (Results).

Statistics

Unpaired Student's T test and Kaplan Meier survival curves were applied using GraphPad Prism software.

Results

The effect of CTLA-4 blockade by mAb UC10 (BMS-863019) in the oxazolone-induced colitis model was evaluated at 2 different dose levels: 20 mg/kg, representing an efficacious dose in mouse tumor models, and at 40 mg/kg. Antibody was administered I.P. every 3 days for 3 doses following epicutaneous delivery of oxazolone. At both dose levels, CTLA-4 mAb exacerbated disease progression as determined by a significant weight loss that resulted in 4 and 6 deaths out of 8 mice for the 20 and 40 mg/kg groups, respectively. At necropsy, the colons of animals treated with CTLA-4 showed hemorrhagic lesions and inflammation, with a severity significantly greater than control mice. Histopathological evaluation showed that CTLA-4-treated mice showed disruption of the normal morphology of the colon with high infiltration of monocytic cells and tissue injury (FIG. 1). Results from this study indicated that oxazolone-induced colitis could be used as a model to study the effect of immunomodulatory agents.

TABLE 1

Effect of CTLA-4 mAb in the Oxazolone-induced Colitis Model

| Group # | Prime Epicutaneous Day 0 | Treatment | Dose (mg/kg) | Study Day | Intrarectal Challenge Day 5 | Dead Mice/ Total |
| --- | --- | --- | --- | --- | --- | --- |
| 1 | 3% Oxazolone | None | | 0 | ETON, 50% | 0/7 |
| 2 | 3% Oxazolone | Control Vehicle (PBS) | 0.2 mL/mouse | 0, 3, 7 | Oxazolone, 0.75% | 2/8 |
| | 3% Oxazolone | Hamster IgG | 20 mg/kg | 0, 3, 7 | Oxazolone, 0.75% | 1/8 |
| 4 | 3% Oxazolone | CTLA-4 mAb | 20 mg/kg | 0, 3, 7 | Oxazolone, 0.75% | 4/8 |
| 5 | 3% Oxazolone | CTLA-4 mAb | 40 mg/kg | 0, 3, 7 | Oxazolone, 0.75% | 6/8 |

Example 3

Method of Assessing the Effect of the Combination of CD137 Agonistic Antibodies with Anti-CTLA4 Blockage on Tumor Growth in a Murine Oxazolone-Induced Colitis Model Since CD137 agonistic mAb can prevent or ameliorate the development of autoimmunity in many experimental mouse models of autoimmune disease (Foell et al., *Ann. NY Acad. Sci.*, 987:230-235 (April 2003); Sun et al., *Nat. Med.*, 8:1405-1413 (2002); Foell et al., *Immunology*, 113(1):89-98 (September 2004); Seo et al., *Nat. Med.*, 10:1088-1094 (2004)), it was of interest to determine if a CD137 agonist antibody (BMS-469492) could modulate the effect of CTLA-4 blockade in immune-mediated colitis models.

Methods

CD137 mAb (BMS-469492, 5 mg/kg, q3dx3) and CTLA-4 mAb (UC10, 20 mg/kg, q3dx3) were administered intraperitoneally on days 0, 3, and 6 after epicutaneous challenge with oxazolone (day 0) alone or in combination. On day 5, animals were re-challenged with 0.75% oxazolone intrarectally. ETOH (ethanol)—treated group did not receive oxazolone. Survival was monitored daily.

Results

In the first study, BMS-469492 (CD137 agonist, 5 mg/kg, administered every 3 days for 3 doses) and mAb CTLA-4 (CTLA-4 blocking mAb, 20 mg/kg, administered every 3 days for 3 doses) were administered alone or concomitantly on days 0, 3, and 6 post-epicutaneous challenge with oxazolone (3%). Mice that received anti-CD137 mAb alone showed improved survival compared with animals treated with CTLA-4 mAb alone ($p<0.01$). As previously observed, anti-CTLA-4 treatment accelerated disease onset and most of the animals died in the first days after antigen challenge. When anti-CD137 mAb was administered at the same time than CTLA-4 mAb, treatments did not exacerbate the disease state compared to the experimental animal group receiving CTLA-4 mAb alone (FIG. 2).

Example 4

Figure 2:
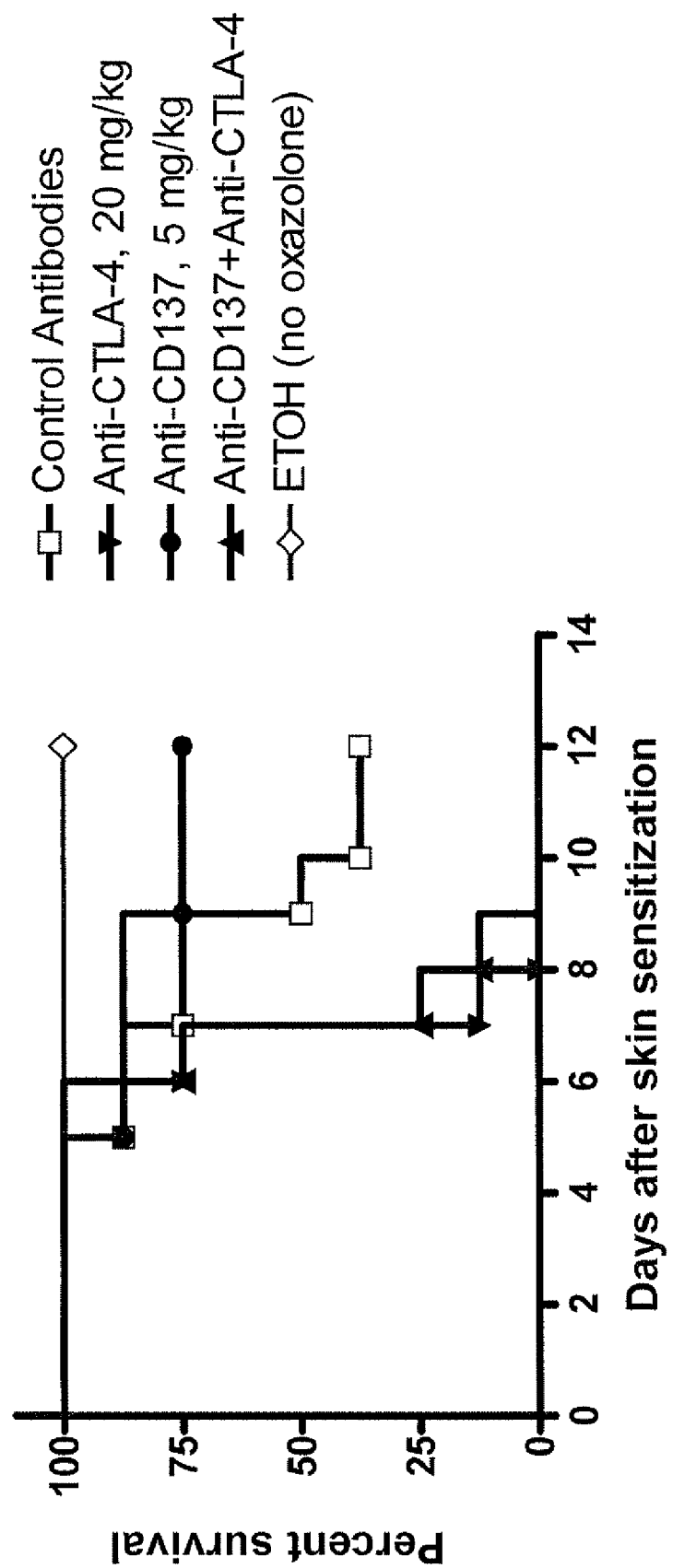
FIG. 2 shows the effect of simultaneous treatment with an agonistic CD137 mAb and CTLA-4 mAb in an oxazolone-induced murine colitis model. CD137 mAb (5 mg/kg, q3dx3) and CTLA-4 mAb (UC10, 20 mg/kg, q3dx3) were administered intraperitoneally on days 0, 3, and 6 after epicutaneous challenge with oxazolone (day 0) alone or in combination. On day 5, animals were re-challenged with 0.75% oxazolone intrarectally. ETOH (ethanol)-treated group did not receive oxazolone. Survival was monitored daily. As shown, mice that received anti-CD137 mAb alone showed improved survival compared with animals treated with CTLA-4 mAb alone (p<0.01). As previously observed, anti-CTLA-4 treatment accelerated disease onset and most of the animals died in the first days after antigen challenge. When anti-CD137 mAb was administered at the same time as CTLA-4 mAb, it did not exacerbate the disease state compared to the experimental animal group receiving CTLA-4 mAb alone.

Method of Assessing Whether the Order in which CD137 Agonistic Antibodies are Administered in Combination with Anti-CTLA4 Blockage has an Effect on Tumor Growth in a Murine Oxazolone-Induced Colitis Model The results summarized in FIG. 2 showed that the CD137 agonistic mAb improved survival compared to the control group. As a consequence, the data suggested that CD137 signaling modulated the severity of the disease. Thus, in the next studies we investigated the effect of CD137 mAb administered prior (18-24 hours earlier) to CTLA-4 mAb.

Methods

Two studies were performed as follows: A) CD137 mAb (BMS-469492, 5 mg/kg, days -1, 2, 5) and CTLA-4 mAb (UC10, 20 mg/kg, days 0, 3, 6) were administered intraperitoneally; B) CTLA-4 mAb was dosed at 10 mg/kg following the same schedule.

For each study, epicutaneous sensitization with oxazolone was performed on day 0 (3%) while intrarectal challenge was done on day 5 (0.75%). ETOH (ethanol)-treated group did not receive oxazolone. Survival was monitored daily.

Results

Figure 3:
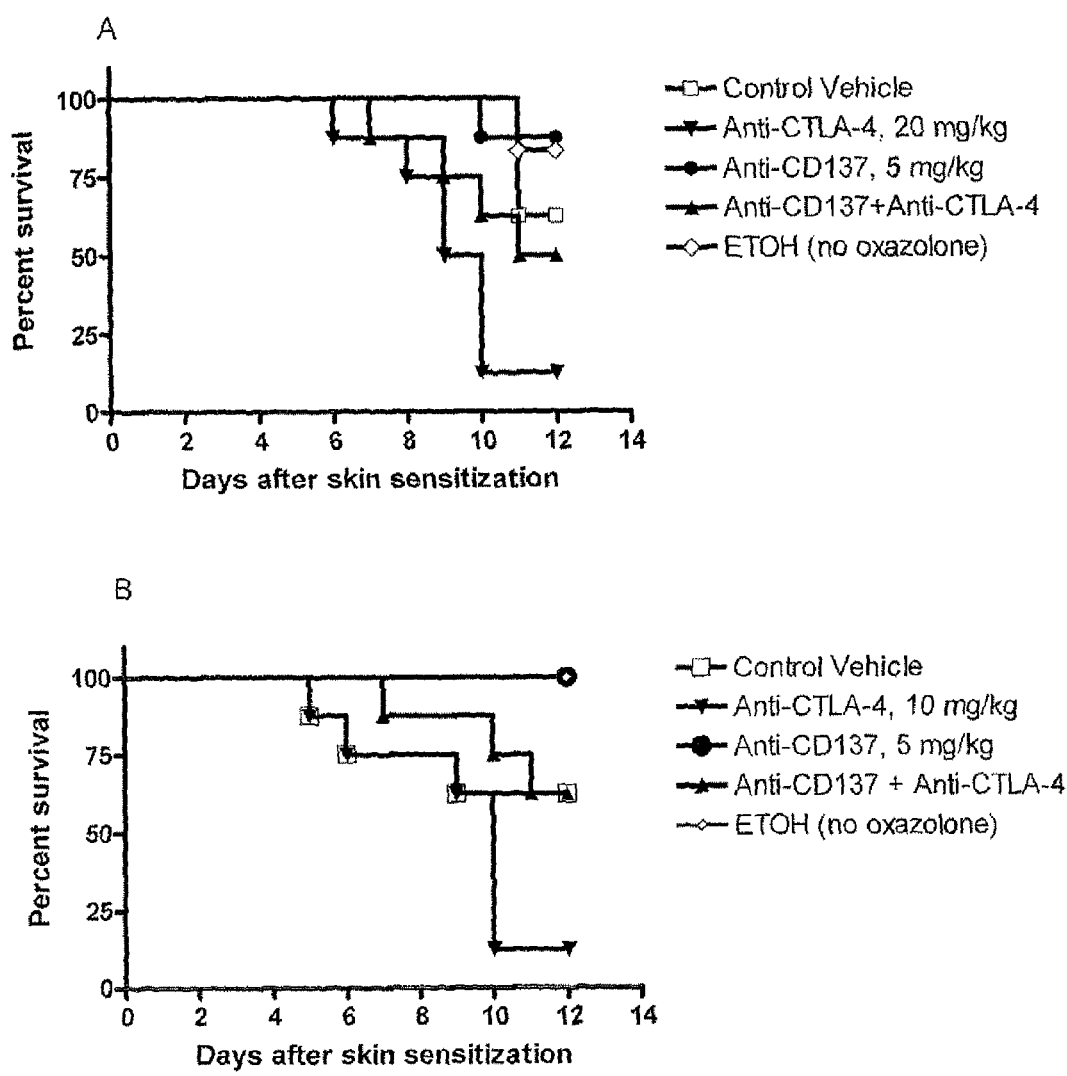
FIG. 3 shows the effect of treatment with CTLA-4 mAb, CD137 mAb, or their combination in an oxazolone-induced colitis murine model when CD137 mAb was administered prior to CTLA-4 mAb. For graph (A), mice were administered intraperitoneally with CD137 mAb (5 mg/kg, days −1, 2, 5) and CTLA-4 mAb (UC10, 20 mg/kg, days 0, 3, 6). For graph (B), mice were dosed with CTLA-4 mAb at 10 mg/kg following the same schedule. Epicutaneous sensitization with oxazolone was performed on day 0 (3%) while intrarectal challenge was done on day 5 (0.75%). ETOH (ethanol) treated group did not receive oxazolone. Survival was monitored daily. In both studies, dosing of CD137 mAb prior to CTLA-4 mAb improved survival compared to CTLA-4 mAb alone (p<0.05).
Figure 4:
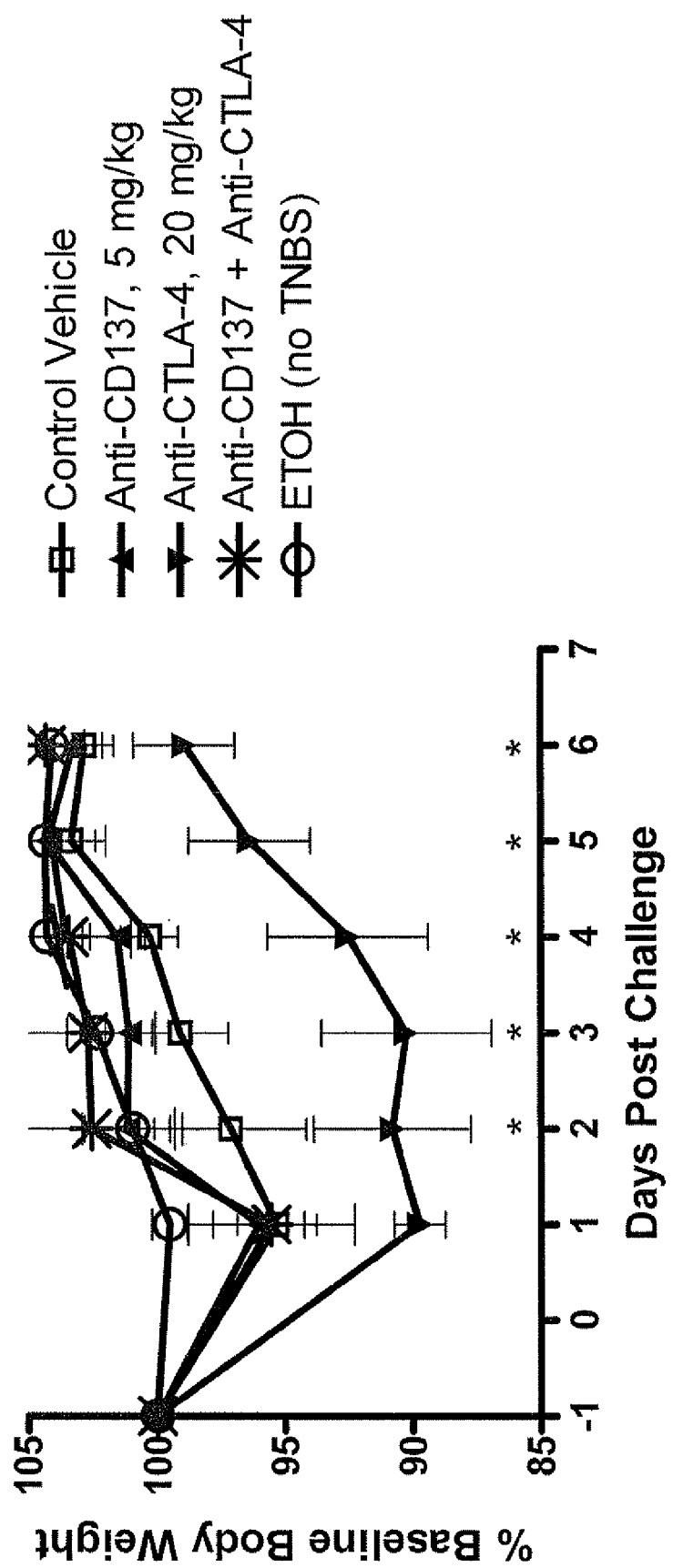
FIG. 4 shows the effect of treatment with CTLA-4 mAb, CD137 mAb or their combination in a TNBS-induced murine colitis model. Mice were treated with CD137 mAb (5 mg/kg) on days −1, 2, and 5, whereas CTLA-4 mAb (20 mg/kg) was administered on days 0, 3, and 6. Intra-rectal injections of TNBS (2 mg/mouse in 35% ethanol) were administered on Day 0 after CTLA-4 mAb treatment. Combination groups followed the same dose and schedule as single agent groups. Mice treated with CTLA-4 mAb produced significant body weight loss compared with control vehicle (p<0.05, days 1-6), whereas CD137 mAb did not. Furthermore, administration of CD137 mAb prior to CTLA-4 mAb prevented the rate of body weight loss observed with CTLA-4 mAb (p<0.05, days 2-6). Animals treated with CTLA-4 mAb, represented by an asterisk ("*"), showed higher % body weight loss compared with animals treated with CD137 mAb+CTLA-4 mAb and CD137 mAb alone (p<0.05, Student's t-test). Data shows mean±SEM of 8 mice/group. Thus, as observed in the oxazolone-based colitis model, CD137 mAb modulated and improved the clinical signs associated with treatment with CTLA-4 mAb in the TNBS-induced colitis model.

In these studies, animals treated with CTLA-4 mAb alone, at either 10 or 20 mg/kg, consistently showed poorer survival compared to control animals, while treatment with the CD137 mAb resulted in a survival rate similar to animals not challenged with oxazolone (ethanol only control group, FIGS. 3A and B). In the combination groups, mice treated with CD137 mAb prior to CTLA-4 mAb (18-24 hours earlier) showed markedly improved survival compared to single agent anti-CTLA-4-treated group (Figures A and B; $p<0.05$). These results indicate that CD137 mAb modulated the severity of the disease induced by CTLA-4 blockade.

Example 5

Method of Assessing the Effect of Combination of CD137 Agonistic Antibodies with Anti-CTLA4 Blockage on Colon Length in a Murine Oxazolone-Induced Colitis Model In an additional study, mice were sacrificed on Day 9 post skin sensitization and colons were removed and measured as an indication of disease severity. As shown in Table 2, colons from animals treated with the combination of CD137 mAb and CTLA-4 mAb were markedly longer than mice treated with CTLA-4 mAb (Table 1).

TABLE 2

Effect of CD137 mAb, CTLA-4 mAb or their Combination on Colon Length in the Oxazolone Colitis Model

| Treatment | Dose | Schedule (Study Days) | Colon Length in mm$^a$ Day 9 (individual measurements in mm) |
|---|---|---|---|
| Control Vehicle | 0.2 mL/mouse | -1, 2, 5<br>0, 3, 6 | 59.5 ± 3.1 (57, 64, 58, 59) |
| CD137 mAb +<br>Control Vehicle | 5 mg/kg<br>0.2 mL/mouse | -1, 2, 5<br>0, 3, 6 | 59.8 ± 6.2 (53, 56, 65, 65) |
| CTLA-4 mAb<br>Control Vehicle | 10 mg/kg<br>0.2 mL/mouse | 0, 3, 6<br>-1, 2, 5 | 51.0 ± 3.6$^b$ (48, 55, 50) |
| CD137 mAb +<br>CTLA-4 mAb | 5 mg/kg<br>10 mg/kg | -1, 2, 5<br>0, 3, 6 | 61.3 ± 7.0$^c$ (63, 64, 51, 67) |
| Control Vehicle<br>No Oxazolone | 0.2 mL/mouse | -1, 2, 5<br>0, 3, 6 | 71.3 ± 6.7 (70, 81, 67, 67) |

$^a$Values represent mean ± SD. Groups consisted of 4 mice, except for CTLA-4 mAb group which had 3 mice. One mouse from this group died before day 9.
$^b$p < 0.05 compared to control vehicle
$^c$p = 0.07 compared to CTLA-4 mAb-treated group. In the combination group CD137 mAb was administered 18 h-24 h prior to CTLA-4 mAb.

Example 6

Method of Assessing the Effect of the Combination of CD137 Agonistic Antibodies with Anti-CTLA4 Blockage on Tumor Growth in a Murine TNBS-Induced Colitis Model The effect of CD137 agonistic mAb in animals treated with CTLA-4 blocking mAb was also evaluated in the TNBS-induced colitis model. Unlike the oxazolone-induced colitis model, mucosal inflammation induced by TNBS results from a Th1 response, mainly driven by IL-12 production. It affects most of the colon, while in the oxazolone-based model inflammation is mainly observed in the distal half of the colon (Strober et al., *Annu. Rev. Immunol.*, 20:495-549 (2002)).

Methods

Mice were treated with CD137 mAb (5 mg/kg) on days −1, 2, and 5, whereas CTLA-4 mAb (20 mg/kg) was administered on days 0, 3, and 6. Intra-rectal injections of TNBS (2 mg/mouse in 35% ethanol) were administered on Day 0 after CTLA-4 mAb treatment. Combination groups followed the same dose and schedule as single agent groups.

Results

Mice treated with CTLA-4 mAb produced significant body weight loss compared with control vehicle (p<0.05, days 1-6), whereas CD137 mAb did not. Furthermore, administration of CD137 mAb prior to CTLA-4 mAb prevented the rate of body weight loss observed with CTLA-4 mAb (p<0.05, days 2-6).

Thus, as observed in the oxazolone-based colitis model, CD137 mAb modulated and improved the clinical signs associated with treatment with CTLA-4 mAb in the TNBS-induced colitis model.

Example 7

Method of Assessing the Effect of Combination of CD137 Agonistic Antibodies with Anti-CTLA4 Blockage on Colon Length in a Murine TNBS-Induced Colitis Model In another study, mice were sacrificed on Day 4 following intrarectal administration of TNBS and colons were removed and their length measured as an indication of disease severity. Day 4 was selected since it was expected to coincide with disease progression.

As shown in Table 3, colons from animals treated with the combination of CD137 mAb and CTLA-4 mAb were markedly longer than mice treated with CTLA-4 mAb.

TABLE 3

Effect of CD137 mAb, CTLA-4 mAb or their Combination on Colon Length in the TNBS Colitis Model

| Treatment | Dose | Schedule (Study Days) | Colon Length in mm$^a$ Day 4 (individual measurements in mm) |
|---|---|---|---|
| Control Vehicle | 0.2 mL/mouse | −1, 2 0, 3 | 64 ± 6.6 (63.58.71) |
| CD137 mAb + Control Vehicle | 5 mg/kg 0.2 mL/mouse | −1, 2 0, 3 | 78.5 ± 6.5 (72, 74, 83, 85) |
| CTLA-4 mAb Control Vehicle | 20 mg/kg 0.2 mL/mouse | 0, 3 −1, 2 | 61.0 ± 8.4 (71, 54, 58) |
| CD137 mAb + CTLA-4 mAb | 5 mg/kg 20 mg/kg | −1, 2 0, 3 | 74.7 ± 5.1 (79, 69, 76)$^b$ |
| Control Vehicle No TNBS | 0.2 mL/mouse | −1, 2 0, 3 | 70.0 ± 2.2 67, 70, 72, 71) |

$^a$Values represent mean ± SD. Groups consisted of 3-4 mice as shown.
$^b$p = 0.08 compared to CTLA-4 mAb alone

Conclusion

In both models of immune-mediated colitis, treatment with an anti-CD137 agonistic mAb prior to treatment with CTLA-4 mAb significantly reduced the clinical signs associated with CTLA-4 mAb treatment. Further studies will be necessary to dissect the immune events responsible for the modulatory effect of CD137 mAb.

The present invention is not limited to the embodiments specifically described above, but is capable of variation and modification without departure from the scope of the appended claims.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, GENBANK® Accession numbers, SWISS-PROT® Accession numbers, or other disclosures) in the Background of the Invention, Detailed Description, Brief Description of the Figures, and Examples is hereby incorporated herein by reference in their entirety. Further, the hard copy of the Sequence Listing submitted herewith, in addition to its corresponding Computer Readable Form, are incorporated herein by reference in their entireties.

What is claimed is:

1. A method for diminishing the incidence or severity of immunotherapy-dependent colitis associated with anti-CTLA4 therapy comprising administering to a mammal in need thereof a combination comprising the sequential administration of a therapeutically effective amount of an agonistic CD137 antibody, followed by the administration of a therapeutically effective amount of an antagonistic CTLA-4 antibody, wherein the incidence or severity of immunotherapy-dependent colitis associated with anti-CTLA4 therapy is diminished.

2. The method according to claim 1 comprising an interstitial period in between said administrations.

3. The method according to claim 2 wherein said interstitial period is one day.

4. The method according to claim 2 wherein said interstitial period is between 18 to 24 hours.

5. The method according to claim 2 wherein said interstitial period is between 12 to 18 hours.

6. The method according to claim 2 wherein said interstitial period is less than 12 hours.

7. The method according to claim 1 wherein the antagonistic CTLA-4 antibody is ipilimumab.

8. The method according to claim 1 wherein the antagonistic CTLA-4 antibody is tremelimumab.

* * * * *

SEQUENCE LISTING

<160> NUMBER OF SEQ ID NOS: 6

<210> SEQ ID NO 1
<211> LENGTH: 9
<212> TYPE: PRT
<213> ORGANISM: Homo sapiens

<400> SEQUENCE: 1

Ile Met Asp Gln Val Pro Phe Ser Val
1               5

<210> SEQ ID NO 2
<211> LENGTH: 9
<212> TYPE: PRT
<213> ORGANISM: Homo sapiens

<400> SEQUENCE: 2

Tyr Leu Glu Pro Gly Pro Val Thr Val
1               5

<210> SEQ ID NO 3
<211> LENGTH: 236
<212> TYPE: PRT
<213> ORGANISM: Homo sapiens

<400> SEQUENCE: 3

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Pro Ala Leu Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 4
<211> LENGTH: 467
<212> TYPE: PRT
<213> ORGANISM: Homo sapiens

<400> SEQUENCE: 4

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Ser Pro Glu Lys Gly Leu
    50                  55                  60

Glu Trp Ile Gly Glu Ile Asn His Gly Gly Tyr Val Thr Tyr Asn Pro
65                  70                  75                  80

Ser Leu Glu Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Tyr Gly Pro Gly Asn Tyr Asp Trp Tyr Phe Asp
        115                 120                 125

Leu Trp Gly Arg Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
```

```
                    385                 390                 395                 400
Trp Glu Ser Asn Gly Gln Pro Glu Asn Tyr Lys Thr Thr Pro Pro
                405                 410                 415

Val Leu Asp Ser Asp Gly Ser Phe Phe Leu Tyr Ser Arg Leu Thr Val
                420                 425                 430

Asp Lys Ser Arg Trp Gln Glu Gly Asn Val Phe Ser Cys Ser Val Met
                435                 440                 445

His Glu Ala Leu His Asn His Tyr Thr Gln Lys Ser Leu Ser Leu Ser
                450                 455                 460

Leu Gly Lys
465

<210> SEQ ID NO 5
<211> LENGTH: 108
<212> TYPE: PRT
<213> ORGANISM: Homo sapiens

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Phe Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 6
<211> LENGTH: 118
<212> TYPE: PRT
<213> ORGANISM: Homo sapiens

<400> SEQUENCE: 6

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
            115
```